(12) United States Patent
Webster et al.

(10) Patent No.: US 10,907,008 B2
(45) Date of Patent: Feb. 2, 2021

(54) HIGHLY FUNCTIONAL EPOXIDIZED RESINS AND COATINGS

(71) Applicant: NDSU RESEARCH FOUNDATION, Fargo, ND (US)

(72) Inventors: Dean C. Webster, Fargo, ND (US); Partha Pratim Sengupta, Fargo, ND (US); Zhigang Chen, Pleasant Prairie, WI (US); Xiao Pan, Shenyang (CN); Adlina Paramarta, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 16/395,304

(22) Filed: Apr. 26, 2019

(65) Prior Publication Data

US 2019/0248952 A1 Aug. 15, 2019

Related U.S. Application Data

(63) Continuation of application No. 14/801,306, filed on Jul. 16, 2015, now Pat. No. 10,329,377, which is a
(Continued)

(51) Int. Cl.
*C08G 59/02* (2006.01)
*C08G 59/34* (2006.01)
(Continued)

(52) U.S. Cl.
CPC ......... *C08G 59/027* (2013.01); *C07D 303/16* (2013.01); *C08G 59/02* (2013.01);
(Continued)

(58) Field of Classification Search
CPC .................................................. C08G 59/027
See application file for complete search history.

(56) References Cited

U.S. PATENT DOCUMENTS 3,209,015 A  9/1965  Wilbur
3,223,657 A  12/1965  Weisfeld et al.
(Continued)

FOREIGN PATENT DOCUMENTS

WO  2011/097484 A1  8/2011

OTHER PUBLICATIONS

International Search Report and Written Opinion for PCT International Application No. PCT/US2011/023753, dated Apr. 6, 2011.
(Continued)

*Primary Examiner* — Megan McCulley
(74) *Attorney, Agent, or Firm* — J.A. Lindeman & Co. PLLC

(57) ABSTRACT

The invention provides highly functional epoxy resins that may be used themselves in coating formulations and applications but which may be further functionalized via ring-opening reactions of the epoxy groups yielding derivative resins with other useful functionalities. The highly functional epoxy resins are synthesized from the epoxidation of vegetable or seed oil esters of polyols having 4 or more hydroxyl groups/molecule. In one embodiment, the polyol is sucrose and the vegetable or seed oil is selected from corn oil, castor oil, soybean oil, safflower oil, sunflower oil, linseed oil, tall oil fatty acid, tung oil, vernonia oil, and mixtures thereof. Methods of making of the epoxy resin and each of its derivative resins are disclosed as are coating compositions and coated objects using each of the resins.

23 Claims, 5 Drawing Sheets

Related U.S. Application Data continuation of application No. 13/577,043, filed as application No. PCT/US2011/023753 on Feb. 4, 2011, now Pat. No. 9,096,773.

(60) Provisional application No. 61/302,124, filed on Feb. 6, 2010, provisional application No. 61/355,453, filed on Jun. 16, 2010, provisional application No. 61/355,487, filed on Jun. 16, 2010, provisional application No. 61/435,338, filed on Jan. 23, 2011.

(51) Int. Cl.

| | | |
|---|---|---|
| *C08G 59/42* | (2006.01) | |
| *C08L 63/00* | (2006.01) | |
| *C08L 63/10* | (2006.01) | |
| *C08G 59/14* | (2006.01) | |
| *C08G 59/16* | (2006.01) | |
| *C08G 59/17* | (2006.01) | |
| *C09D 163/00* | (2006.01) | |
| *C07D 303/16* | (2006.01) | |
| *C09D 163/08* | (2006.01) | |
| *C09D 175/08* | (2006.01) | |

(52) U.S. Cl.
CPC ..... *C08G 59/1438* (2013.01); *C08G 59/1455* (2013.01); *C08G 59/1466* (2013.01); *C08G 59/34* (2013.01); *C08G 59/4207* (2013.01); *C08G 59/4215* (2013.01); *C08G 59/4223* (2013.01); *C08L 63/00* (2013.01); *C08L 63/10* (2013.01); *C09D 163/00* (2013.01); *C09D 163/08* (2013.01); *C09D 175/08* (2013.01)

(56) References Cited

U.S. PATENT DOCUMENTS

| | | | |
|---|---|---|---|
| 3,236,795 A | 2/1966 | Graver | |
| 3,248,404 A | 4/1966 | Werdelmann et al. | |
| 3,792,041 A | 2/1974 | Yamagishi et al. | |
| 3,870,664 A | 3/1975 | Faulkner | |
| 4,117,029 A | 9/1978 | Kitano | |
| 4,517,360 A | 5/1985 | Volpenhein | |
| 4,663,072 A | 5/1987 | Cheung | |
| 5,318,808 A | 6/1994 | Crivello et al. | |
| 5,646,226 A | 7/1997 | Sachinala et al. | |
| 6,077,879 A | 6/2000 | Ohtsuki et al. | |
| 6,303,777 B1 | 10/2001 | Kao et al. | |
| 6,518,226 B2 | 2/2003 | Volker | |
| 2002/0013396 A1 | 1/2002 | Benecke et al. | |
| 2003/0229224 A1 | 12/2003 | Schaefer et al. | |
| 2006/0020062 A1 | 1/2006 | Bloom | |
| 2007/0232816 A1 | 10/2007 | Soi | |
| 2009/0005508 A1 | 1/2009 | Bloom | |
| 2009/0286896 A1* | 11/2009 | Roh ........................ | C08G 18/36 |
| | | | 521/159 |
| 2010/0009104 A1 | 1/2010 | Greelis et al. | |
| 2011/0073253 A1 | 3/2011 | Clausi et al. | |
| 2013/0136931 A1 | 5/2013 | James et al. | |
| 2013/0203935 A1 | 8/2013 | Thiele et al. | |

OTHER PUBLICATIONS

International Search Report and Written Opinion in PCT Application No. PCT/US2014/066073 dated Feb. 23, 2015.

Busnel et al.: "Improvement of the Processing of Polyurethane Reinforced by Glass and Cellulosic Fibres," Thermosets 2011—From Monomers to Components, Proceedings of the 2nd International Conference on Thermosets, Sep. 21, 2011, 1-5, 2011. [retrieved on Jan. 12, 2015]. Retrieved from the Internet <URL: http://nparc.cisti-icist.nrc-cnrc.gc.ca/npsi/ctrl?action=rtdoc&an=18929686&lang=en>.

Hosseini et al.: "Utilization of Flax Fibers and Glass Fibers in a Bio-Based Resin," The 19th International Conference on Composite Materials 2013, 565-572, Jul. 20-Aug. 2, 2013. [retrieved on Jan. 12, 2015]. Retrieved from the Internet. <URL: http://www.researchgate.net/publication/266910697_Utilization_of_flax_fibers_and_glass_fibers_in_a_bio-based_resin>.

\* cited by examiner

PHOTO-DSC OF FORMULATION CONTAINING ESE/ ESO (SET I)

PHOTO-DSC OF FORMULATION CONTAINING ESE/ ESO AND UVR 6110 (SET II)

HIGHLY FUNCTIONAL EPOXIDIZED RESINS AND COATINGS

CROSS-REFERENCE TO RELATED APPLICATIONS

This application is a Continuation of application Ser. No. 14/801,306, filed Jul. 16, 2015; which is a Continuation of application Ser. No. 13/577,043, now U.S. Pat. No. 9,096,773; which claims priority to PCT International Application No. PCT/US2011/023753, filed Feb. 4, 2011; which claims priority to U.S. Application 61/302,124, filed Feb. 6, 2010; U.S. Application 61/355,453, filed Jun. 16, 2010; U.S. Application 61/355,487, filed Jun. 16, 2010; and U.S. Application 61/435,338, filed Jan. 23, 2011; each of which is incorporated herein by reference.

STATEMENT OF GOVERNMENT SUPPORT

This invention was made with government support under grant no. 2007-38202-18597 awarded by the US Department of Agriculture (USDA). The US Government has certain rights in the invention.

BACKGROUND

The utilization of renewable raw materials has been considered as one of the "green chemistry" approaches that can contribute to sustainable development. Metzger, et al., *C. R. Chim.*, 2004, 7, 569. Plant oils, naturally occurring triglycerides of fatty acids, make up the greatest proportion of the current consumption of renewable feedstocks used to prepare biobased polymers. Meier, et al., *Chem. Soc. Rev.*, 2007, 36, 1788; Baumann, et al., *Angew. Chem. Int. Ed. Engl.* 1998, 27, 41; Biermann, et al., *Angew. Chem. Int. Ed.*, 2000, 39, 2206; Khot, et al., *J. Appl. Polym. Sci.*, 2001, 82, 703. Carbohydrates are another important class of renewable sources of green materials, and the versatile industrial work of transforming low molecular weight carbohydrates (e.g. mono- and di-saccharides) into products as the potential to replace petrochemical products is very attractive. F. W. Lichtenthaler and S. Peters, *C. R. Chim.*, 2004, 7, 65-90.

Cationic UV curable coatings account for only about 8% of all the UV-coatings used in industry (Gu, et al., *J. Coat. Technol.* 2002, 74, 49.) primarily due to fewer types of cationic polymerizable monomers and oligomers available in the market (Zou, et al., *Macromol. Chem. Phys.* 2005, 206, 967). The three major types of epoxides used are silicon-containing epoxides, epoxidized seed oils (soybean or linseed oils) and cycloaliphatics. The seed oil epoxides are synthesized from renewable natural resources. A factor that prevents the extensive use of epoxidized oils is the relative low reactivity of the internal epoxy groups (Zou, et al., *Macromol. Chem. Phys.* 2005, 206, 967 and Sangermano, et al., *J. Mater. Sci.* 2002, 37, 4753). There remains, however, a need to explore new processes to broaden the applications of the seed oil epoxides. In recent years there has been growing interest in using vegetable oils as raw materials in resin production.

Vegetable oils are derived from the seeds of various plants and are chemically triglycerides of fatty acids. That is, vegetable oils consist of three moles of fatty acids esterified with one mole of glycerol. As shown below in Formula I, fatty acids are linear carboxylic acids having 4 to 28 carbons and may be saturated or ethylenically unsaturated.

Formula I

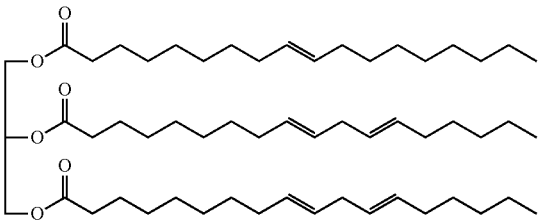

Different plants produce oils having differing compositions in the fatty acid portion of the oil. Naturally-occurring vegetable oils are by definition mixtures of compounds, as are the fatty acids comprising them. They are usually either defined by their source (soybean, linseed) or by their fatty acid composition. A primary variable that differentiates one vegetable oil from another is the number of double bonds in the fatty acid; however, additional functional groups can be present such as hydroxyl groups in castor oil and epoxide groups in vernonia oil. Table 1 below identifies the typical fatty acid composition for some commonly occurring vegetable oils.

TABLE 1

| | Fatty Acid | Unsaturation | Coconut | Corn | Soybean | Safflower | Sunflower | Linseed | Castor | Tall Oil FA | Tung |
|---|---|---|---|---|---|---|---|---|---|---|---|
| $C_{12}$ | Lauric | 0 | 44 | | | | | | | | |
| $C_{14}$ | Myristic | 0 | 18 | | | | | | | | |
| $C_{16}$ | Palmitic | 0 | 11 | 13 | 11 | 8 | 11 | 6 | 2 | 5 | 4 |
| $C_{18}$ | Stearic | 0 | 6 | 4 | 4 | 3 | 6 | 4 | 1 | 3 | 1 |
| | Oleic | 1 | 7 | 29 | 25 | 13 | 29 | 22 | 7 | 46 | 8 |
| | Ricinoleic | 1 | | | | | | | 87 | | |
| | Linoleic | 2 | 2 | 54 | 51 | 75 | 52 | 16 | 3 | 41 | 4 |
| | Linolenic | 3 | | | 9 | 1 | 2 | 52 | | 3 | 3 |
| | Eleaosteric | 3 | | | | | | | | | 80 |
| Iodine Value | | | 7.5-10.5 | 103-128 | 120-141 | 140-150 | 125-136 | 155-205 | 81-91 | 165-170 | 160-175 |

Vegetable oils have been used extensively as binder systems in paints and coatings for centuries. Drying oils, such as linseed oil, have been used as a component of paint binders since drying oils can be converted into a tack free film upon reaction with atmospheric oxygen in a process called autoxidation. Vegetable oils have also been used in the synthesis of alkyd resins by combining the fatty acids in the oils with other monomers to form a fatty acid containing polyester resin. Vegetable oils also have several advantages of being renewable, biodegradable and hence have less impact on the environment. Vegetable oils can impart desirable flexibility and toughness to the otherwise brittle cycloaliphatic epoxide system. Wan Rosli, et al., *Eur. Polym. J.* 2003, 39, 593.

Sucrose, β-D-fructofuranosyl-α-D-glucopyranoside, is a disaccharide having eight hydroxyl groups. The combination of sucrose and vegetable oil fatty acids to yield sucrose esters of fatty acids (SEFA) as coating vehicles was first explored in the 1960s. Bobalek, et al., *Official Digest,* 1961, 453; Walsh, et al., *Div. Org. Coatings Plastic Chem.,* 1961, 21, 125. However, in these early studies, the maximum degree of substitution (DS) was limited to about 7 of the available 8 hydroxyl groups. The resins do not appear to have been commercialized at that time. In the early 2000s, Proctor & Gamble (P&G) Chemicals developed an efficient process for industrially manufacturing SEFAs commercially under the brand name SEFOSE with a high DS of at least 7.7 (representing a mixture of sucrose hexa, hepta, and octaesters, with a minimum of 70% by weight octaester) (U.S. Pat. Nos. 6,995,232; 6,620,952; and 6,887,947), and introduced them with a focus on marketing to the lubricant and paint industries. Due to their low viscosities (300-400 mPa·s), SEFOSE sucrose esters can be used as binders and reactive diluents for air-drying high solids coatings. Formula II displays the possible molecular structure of a sucrose ester with full substitution. Procter and Gamble has reported a process to prepare highly substituted vegetable oil esters of sucrose using transesterification of sucrose with the methyl esters of sucrose. U.S. Pat. No. 6,995,232.

Formula II

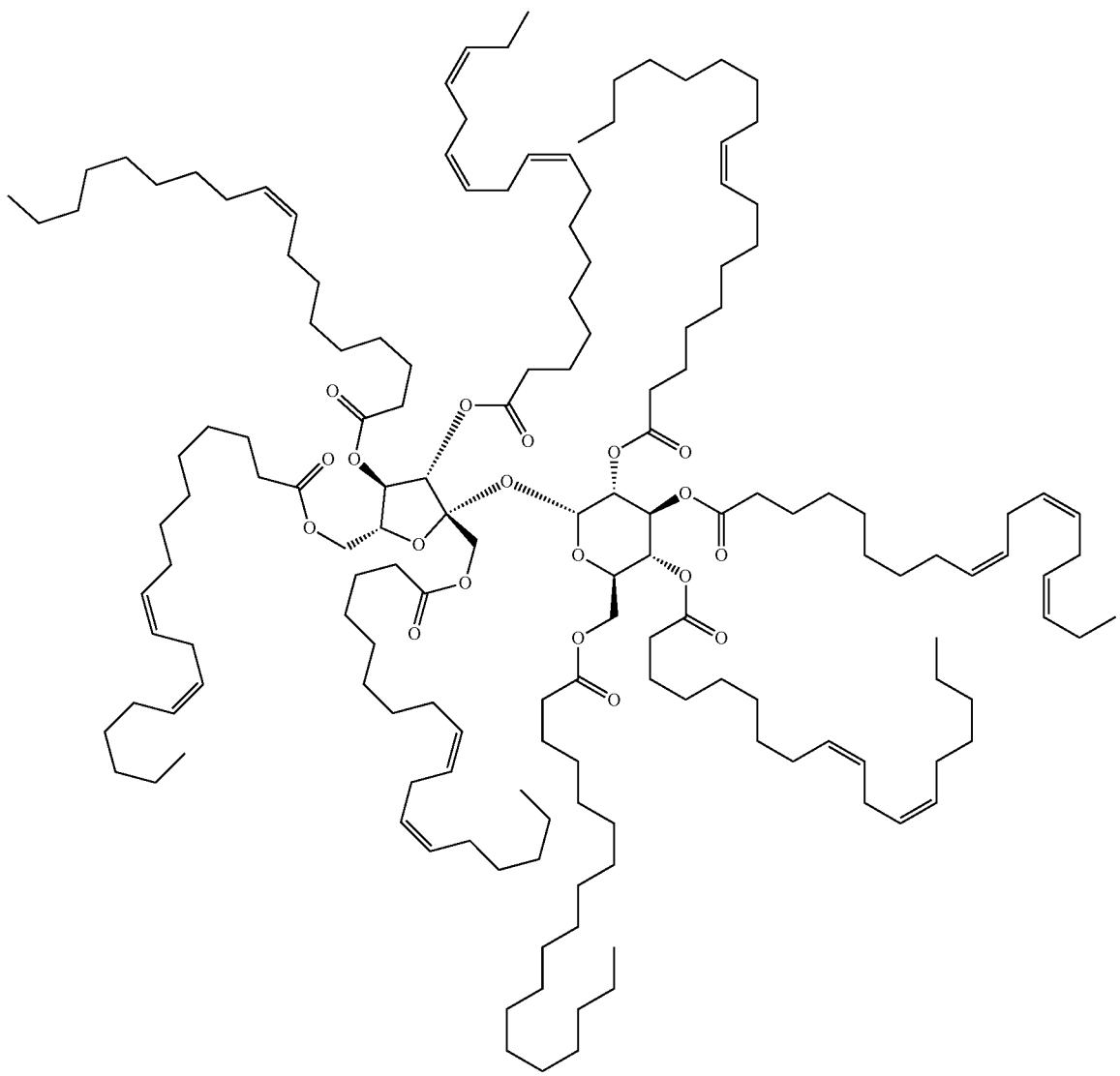

Molecular structure of sucrose ester of fatty acids

An epoxide group is a three-membered, cyclic ether containing two carbon atoms and one oxygen atom. An epoxide can also be called an oxirane. As in known in the art, an epoxy group has the structure shown in formula III in which R and R' are organic moieties representing the remainder of the compound.

Formula III

Epoxy resins are materials consisting of one or more epoxide groups. Due to the strained nature of the oxirane ring, epoxide groups are highly reactive and can be reacted with nucleophiles such as amines, alcohols, carboxylic acids. Thus, epoxy resins having two or more epoxy groups can be reacted with compounds having multiple nucleophilic groups to form highly crosslinked thermoset polymers. Oxiranes can also be homopolymerized. Epoxy resins having two or more epoxy groups can be homopolymerized to form highly crosslinked networks. Crosslinked epoxy resins are used in a large number of applications including coatings, adhesives, and composites, among others. The most commonly used epoxy resins are those made from reacting bisphenol-A with epichlorohydrin to yield difunctional epoxy resins.

Epoxidation is one of the most important and useful modifications using the double bonds of ethylenically unsaturated fatty compounds (Scheme 1 below), since epoxide is a reactive intermediate to readily generate new functional groups. Ring-opening of epoxide via nucleophilic addition leads to a large number of products, such as diol, alkoxy alcohol (ether alcohol), hydroxy ester (ester alcohol), amino alcohol, and others. Through epoxide opening of epoxidized soybean oil using alcohols, triglyceride polyols intended for application in polyurethanes have been successfully prepared by Petrovic and co-works. U.S. Pat. Nos. 6,107,433 and 6,6867,435; and Zlatanić, et al., *J. Polym. Sci., Part B: Polym. Phys.*, 2004, 42, 809.

Epoxide reaction with ethylenically unsaturated acids has been widely utilized to synthesize oil-based free-radical UV-curable coating resins by reacting acrylic acids with epoxidized vegetable oils (EVOs). LaScala, et al., *J. Am. Oil Chem. Soc.*, 2002, 79, 59; LaScala, et al., *Polymer*, 2005, 46, 61; and Pelletier, et al. *J. Appl. Polym. Sci.*, 2006, 99, 3218.

Epoxide groups, or oxirane groups, as discussed, can be synthesized by the oxidation of vinyl groups. Findley, et al., (*JACS*, 67, 412-414 (1945)) reported a method to convert the ethylenically unsaturated groups of triglyceride vegetable oils to epoxy groups, as shown in the scheme below. A number of other processes and catalysts have been developed to also achieve epoxidized oils in good yields.

Scheme 1

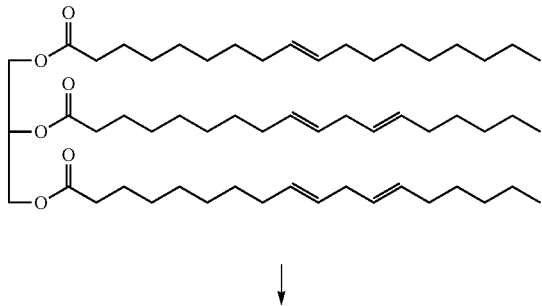

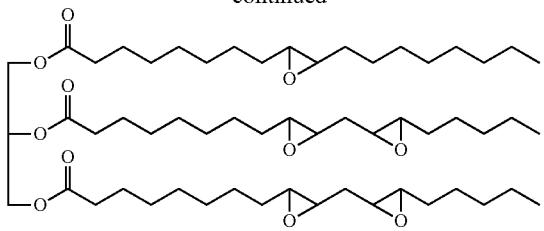

Generally, while there are four techniques that can be employed to produce epoxides from olefinic molecules (Mungroo, et al., *J. Am. Oil Chem. Soc.*, 2008, 85, 887), the in situ performic/peracetic acid (HCOOH or $CH_3COOH$) process appears to be the most widely applied method to epoxidize fatty compounds. Scheme 2 displays the reaction mechanism, which consists of a first step of peroxyacid formation and a second step of double bond epoxidation. Recently, the kinetics of epoxidation of vegetable oils and the extent of side reactions was studied using an acidic ion exchange resin as catalyst and revealed that the reactions were first order with respect to the amount of double bonds and that side reactions were highly suppressed; the conversion of double bonds to epoxides was also high. Petrović, et al., *Eur. J. Lipid Sci. Technol.*, 2002, 104, 293; and Goud, et al., *Chem. Eng. Sci.*, 2007, 62, 4065. The catalyst, Amberlite IR 120, is an acidic ion exchange resin, a copolymer based on styrene (98 wt %) crosslinked by divinylbenzene (2 wt %). Its acidity is generated by sulfonic acid groups attached to the polymer skeleton.

Scheme 2 Reactions mechanism for in situ epoxidation with peroxyacid

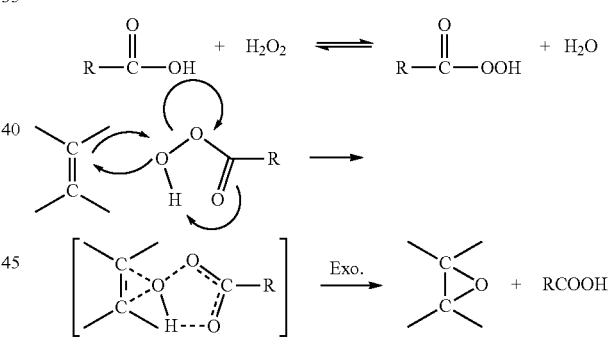

Epoxides generated from the epoxidation of double bonds of ethylenically unsaturated fatty acids are known as internal epoxides—both carbons of the heterocyclic ring are substituted with another carbon. The most commonly used epoxy resins are the bisphenol-A diglycidyl ether resins. The epoxy groups on these resins are of the type known as external epoxides—three of the four substituent groups on the heterocyclic ring are hydrogen atoms. Since internal epoxides are much less reactive than external epoxides in most epoxy curing reactions, the roles traditionally assigned to epoxidized oils are as stabilizers and plasticizers for halogen-containing polymers (i.e. poly(vinyl chloride)) (Karmalm, et al., *Polym. Degrad. Stab.*, 2009, 94, 2275; Fenollar, et al., *Eur. Polym. J.*, 2009, 45, 2674; and Bueno-Ferrer, et al., *Polym. Degrad. Stab.*, 2010, 95, 2207), and reactive toughening agents for rigid thermosetting plastics (e.g. phenolic resins). Miyagawa, et al., *Polym. Eng. Sci.*, 2005, 45, 487. It has also been shown that EVOs can be cured using cationic photopolymerization of epoxides to form coatings. Crivello, et al., *Chem. Mater.*, 1992, 4, 692; Thames, et al., *Surf. Coat. Technol.*, 1999, 115, 208; and Ortiz, et al., *Polymer*, 2005, 46, 1535.

Crivello reported the preparation of a number of epoxidized vegetable oils and their crosslinking using cationic photoinitiators. U.S. Pat. No. 5,318,808; Crivello, et al., *Chem. Mater.*, 1992, 4, 692-699. In general, the coatings formed from photopolymerization were soft due to the low crosslink density obtained and the flexible aliphatic nature of the backbone of the vegetable oils. Epoxy-anhydride curing using epoxidized soybean oil (ESO) and dicarboxylic acid anhydrides in the presence of tertiary amine and imidazole as catalysts have also been studied (Bosch et al., *Polymer Bulletin*, 1993, 31, 679-685; Annelise, et al., *Journal of the American Oil Chemists' Society*, 2002, 79, 797-802) but there remains a need for improved epoxy-anhydride curing compositions.

The radiation curing industry has been using acrylated resins as the key components in coatings and inks. Bajpai, et al., *Pigment & Resin Technology* 2004, 33, 160. Acrylated soybean oils (ASO) takes up 90% of acrylated resin's market consumption due to its low cost and availability. Prantil, B. *Journal of Oil and Colour Chemist's Association* 2000, 83, 460. ASO resin is great for printing ink due to its excellent pigment wetting power. Bajpai, et al., *Pigment & Resin Technology* 2004, 33, 160. Furthermore, the acrylate groups in the molecules are able to participate in free-radical polymerization in the coating system. Bunker, et al., *Journal of Polymer Science: Part A: Polymer Chemistry* 2002, 40, 451-458. A need still remains for improved acrylated resins, particularly resins which can be derived from low-cost and renewable raw materials.

SUMMARY OF THE INVENTION

It has been found that by increasing the functionality of epoxy groups (number of epoxy groups per molecule) using vegetable oil based compounds, the problems of soft crosslinked coatings can be overcome. The invention provides highly functional epoxy resins that may be used themselves in coating formulations and applications but which may be further functionalized via the epoxy groups yielding derivative resins with other useful functionalities.

Highly functional epoxy resins are synthesized from the epoxidation of vegetable or seed oil esters of polyols having 4 or more hydroxyl groups/molecule. The epoxy resins can be cured using UV photoinitiators to hard coatings. The novel epoxy resins can also be incorporated into formulations containing oxetanes, cycloaliphatic epoxides, and polyols. The photopolymerization rate is significantly higher for these novel epoxy resins than a conventional epoxidized vegetable or seed oil.

In one embodiment, the invention relates to an epoxy resin which is the reaction product of a polyol having 4 or more hydroxyl groups; and an ethylenically unsaturated fatty acid, optionally a saturated fatty acid, or mixtures thereof; where at least one ethylenically unsaturated group of the ethylenically unsaturated fatty acid is oxidized to an epoxy group. The polyol having 4 or more hydroxyl groups may be, for example, pentaerythritol, di-trimethylolpropane, di-pentaerythritol, tri-pentaerythritol, sucrose, glucose, mannose, fructose, galactose, raffinose, copolymers of styrene and allyl alcohol, polyglycidol and poly(dimethylolpropionic acid); and the ethylenically unsaturated fatty acid, optionally a saturated fatty acid, or mixtures thereof may be a vegetable or seed oil. In one embodiment, the polyol is sucrose and the vegetable or seed oil is selected from coconut oil, corn oil, castor oil, soybean oil, safflower oil, sunflower oil, linseed oil, tall oil fatty acid, tung oil, vernonia oil, and mixtures thereof. In one embodiment, the polyol is sucrose and the oil is soybean oil. The degree of esterification may be varied. The polyol may be fully esterified, where substantially all of the hydroxyl groups have been esterified with the fatty acid, or it may be partially esterified, where only a fraction of the available hydroxyl groups have been esterified. Similarly, the degree of epoxidation may be varied from substantially all to a fraction of the available double bonds.

The epoxy resins of the invention may be derivatized by ring-opening reactions of at least a portion of the epoxy groups to form resins having different functional groups. In one embodiment, the epoxy resin is reacted with an ethylenically unsaturated acid to introduce ethylenically unsaturated groups. A resin having hydroxyl functionality is another embodiment of the invention which is the reaction product of an epoxy resin of the invention and at least one organic acid or at least one alcohol. The degree of derivatization may also be varied. In some embodiments substantially all of the epoxy groups may be derivatized while in others only a fraction of the available epoxy groups may be derivatized.

Methods of making of the epoxy resin, and each of its derivative resins, are separate embodiments of the invention. Coating compositions and coated objects using each of the resins are further embodiments of the invention. An epoxy-anhydride composition, a further embodiment of the invention, comprises an epoxy resin of the invention, an acid anhydride, and a tertiary amine catalyst.

BRIEF DESCRIPTIONS OF THE FIGURES

DESCRIPTION OF THE INVENTION

Figure 1:
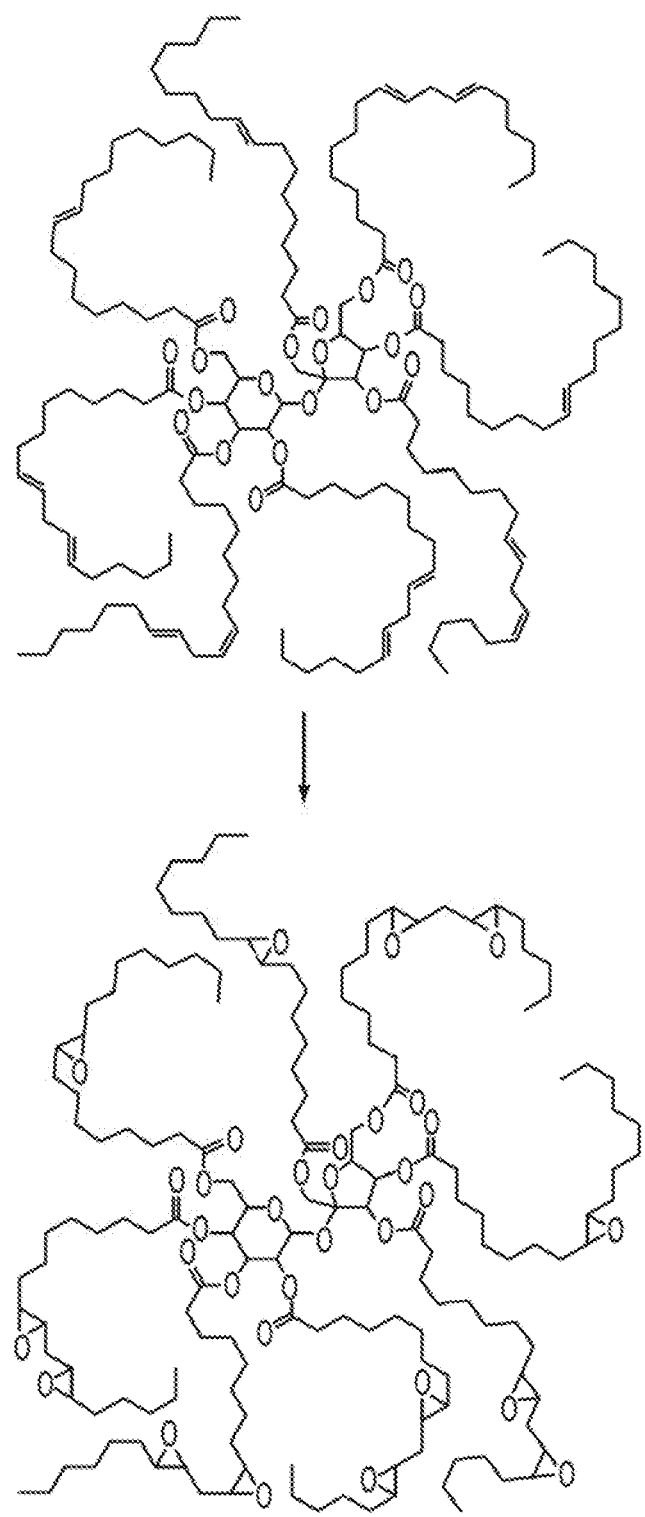
FIG. 1 depicts an exemplary epoxidation of a sucrose fatty acid ester according to the invention.

Highly functional epoxy resins of the invention are prepared from the epoxidation of vegetable oil fatty acid esters of polyols having >4 hydroxyl groups/molecule. Polyol esters of fatty acids, PEFA's, containing four or more vegetable oil fatty acid moieties per molecule can be synthesized by the reaction of polyols with 4 or more hydroxyl groups per molecule with either a mixture of fatty acids or esters of fatty acids with a low molecular weight alcohol, as is known in the art. The former method is direct esterification while the latter method is transesterification. A catalyst may be used in the synthesis of these compounds. As shown in FIG. 1 with sucrose, as an exemplary polyol to be used in the invention, esterified with a vegetable oil fatty acid, epoxide groups may then be introduced by oxidation of the vinyl groups in the vegetable oil fatty acid to form epoxidized polyol esters of fatty acids, EPEFA's. The epoxidation may be carried out using reactions known in the art for the oxidation of vinyl groups with in situ epoxidation with peroxyacid being a preferred method.

Polyols having at least 4 hydroxyl groups per molecule suitable for the process include, but are not limited to, pentaerythritol, di-trimethylolpropane, di-pentaerythritol, tri-pentaerythritol, sucrose, glucose, mannose, fructose, galactose, raffinose, and the like. Polymeric polyols can also be used including, for example, copolymers of styrene and allyl alcohol, hyperbranched polyols such as polyglycidol and poly(dimethylolpropionic acid), and the like. Exemplary polyols are shown below in Scheme 3 with the number of hydroxyl groups indicated by (f). Comparing sucrose to glycerol, there are a number of advantages for the use of a polyol having more than 4 hydroxyl groups/molecule including, but not limited to, a higher number of fatty acids/molecule; a higher number of unsaturations/molecule; when epoxidized, a higher number of oxiranes/molecule; and when crosslinked in a coating, higher crosslink density.

The degree of esterification may be varied. The polyol may be fully esterified, where substantially all of the hydroxyl groups have been esterified with the fatty acid, or it may be partially esterified, where only a fraction of the available hydroxyl groups have been esterified. It is understood in the art that some residual hydroxyl groups may remain even when full esterification is desired. In some applications, as discussed below, residual hydroxyl groups may provide benefits to the resin. Similarly, the degree of epoxidation may be varied from substantially all to a fraction of the available double bonds. The variation in the degree of esterification and/or epoxidation permits one of ordinary skill to select the amount of reactivity in the resin, both for the epoxidized resins and their derivatives.

Scheme 3

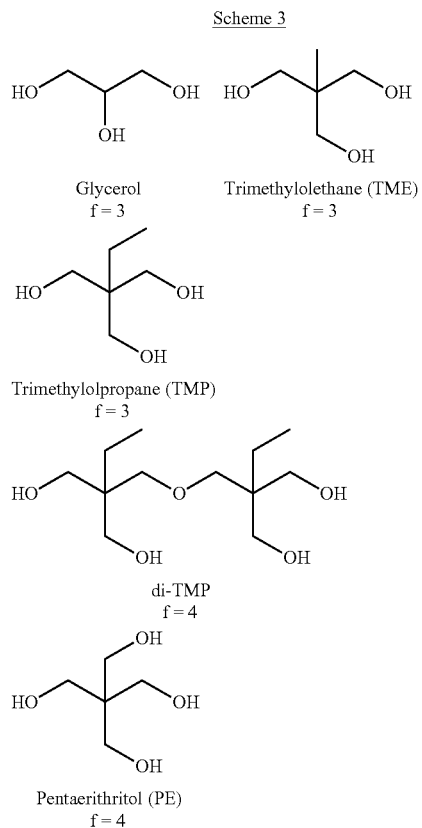

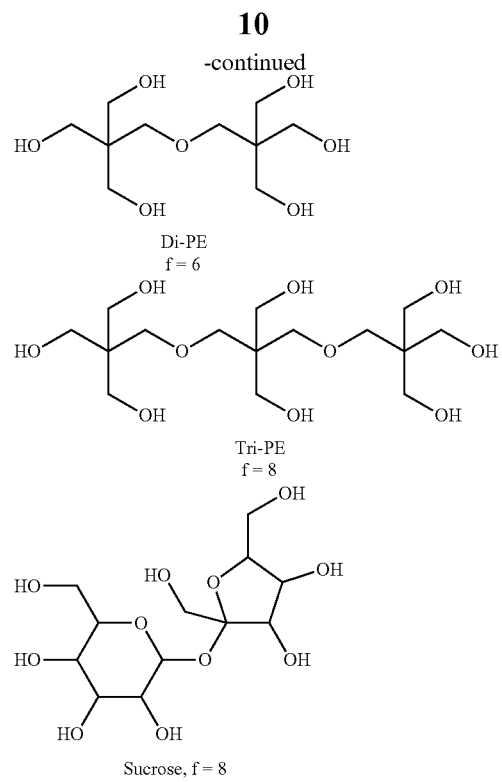

The hydroxyl groups on the polyols can be either completely reacted or only partially reacted with fatty acid moieties. Any ethylenically unsaturated fatty acid may be used to prepare a polyol ester of fatty acids to be used in the invention, with polyethylenically unsaturated fatty acids, those with more than one double bond in the fatty acid chain, being preferred. The Omega 3, Omega 6, and Omega 9 fatty acids, where the double bonds are interrupted by methylene groups, and the seed and vegetable oils containing them may be used to prepare polyol ester of fatty acids to be used in the invention. Mixtures of fatty acids and of vegetable or seed oils, plant oils, may be used in the invention. The plant oils, as indicated above, contain mixtures of fatty acids with ethylenically unsaturated and saturated fatty acids possibly present depending on the type of oil. Examples of oils which may be used in the invention, include but are not limited to, corn oil, castor oil, soybean oil, safflower oil, sunflower oil, linseed oil, tall oil fatty acid, tung oil, vernonia oil, and mixtures thereof. As discussed above, the polyol fatty acid ester may be prepared by direct esterification of the polyol or by transesterification as is known in the art. The double bonds on the fatty acid moieties may be converted into epoxy groups using known oxidation chemistry yielding highly functional epoxy resins, EPEFA's—epoxidized polyol esters of fatty acids. Table 2 lists the double bond functionality of some representative fatty acid esters (=/FA) based upon the number of esterified hydroxyl groups (f).

TABLE 2

Double Bond Functionality of Fatty Acids in Selected Oils

| Oil | Avg. =/FA | Functionality of = for FA esters having the indicated FA functionality | | | |
| --- | --- | --- | --- | --- | --- |
| | | f = 3 | f = 4 | f = 6 | f = 8 |
| Soybean | 1.54 | 4.62 | 6.16 | 9.24 | 12.32 |
| Safflower | 1.66 | 4.98 | 6.64 | 9.96 | 13.28 |
| Sunflower | 1.39 | 4.17 | 5.56 | 8.34 | 11.12 |

TABLE 2-continued

Double Bond Functionality of Fatty Acids in Selected Oils

| Oil | Avg. =/ FA | Functionality of = for FA esters having the indicated FA functionality | | | |
|---|---|---|---|---|---|
| | | f = 3 | f = 4 | f = 6 | f = 8 |
| Linseed | 2.10 | 6.30 | 8.40 | 12.60 | 16.80 |
| Tall Oil Fatty Acid | 1.37 | 4.11 | 5.48 | 8.22 | 10.96 |

Figure 2A:
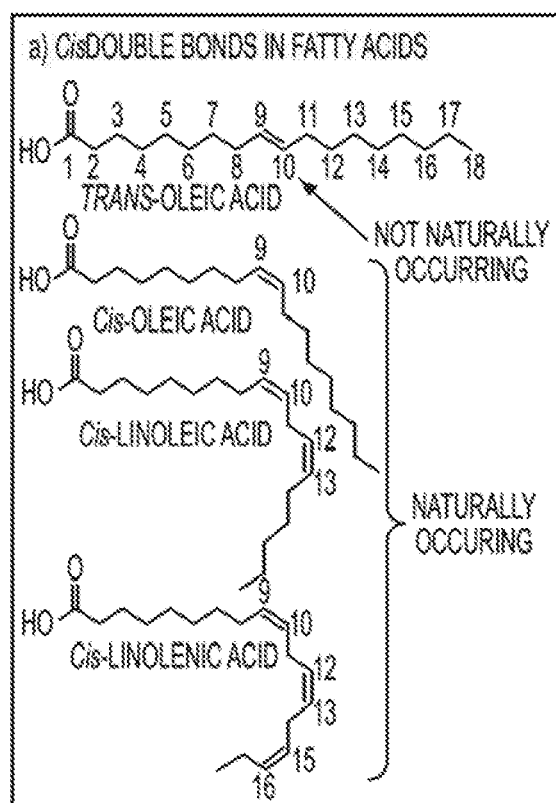
FIGS. 2A and 2B show the effect of cis configuration of double bonds and epoxides on fatty acid morphology.
Figure 2B:
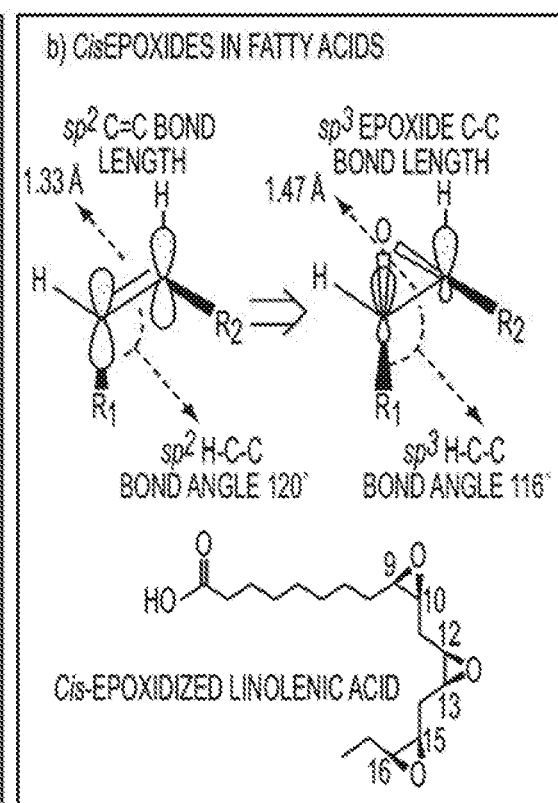

The geometry of the double bonds in naturally occurring plant oil fatty acids are in the cis configuration, in which the adjacent hydrogen atoms are on the same side of the double bond. One interesting feature of the double bond in these ethylenically unsaturated fatty acid chains is that it puts a "kink" in the chain (FIG. 2a). For example, linolenic acid can be significantly bent by three "kinks" of three cis double bonds. Peroxyacids transfer oxygen to the double bonds with syn stereochemistry. The reaction is stereospecific, in which cis double bonds yield cis epoxides. The main effect of epoxidation on the alkene carbons is to transform their hybridization from $sp^2$ to $sp^3$ (FIG. 2b).

The polyol esters used in the invention, and particularly sucrose esters, have compact macromolecular structures, due to the compact structure of the polyol core and the generally uniform distribution of fatty acids around the core. Since the presence of cis double bonds and epoxides can vary the extension of the fatty acid chains, the amount of double bonds and epoxides surely influences the overall dimension of sucrose ester macromolecules. Therefore, the morphology of sucrose esters is influenced by the morphology of its up to eight fatty acid chains.

A dilute solution of polyol ester molecules, such as sucrose ester molecules, can be thought of as their equivalent spheres. They are uniform, rigid, and non-interacting. For example, the intrinsic viscosity of sucrose esters reflects the hydrodynamic volume of their equivalent spheres. For fully substituted sucrose esters, it was found that 1) epoxidized sucrose esters have higher intrinsic viscosities than their corresponding sucrose esters, and 2) higher amounts of epoxide result in higher intrinsic viscosities. These observations indicate that the hydrodynamic volume of the sucrose ester molecules is increased by epoxidation and that the higher epoxide content results in larger dimension molecules.

In addition to the larger volume for the epoxidized polyol esters, intermolecular forces, such as van der Waals forces and dipole-dipole interactions, can be invoked for understanding the observations of bulk viscosity and density of the sucrose esters. Not only does epoxidation increase the molecular weight of polyol esters, the polarity of the polyol esters also increases. Thus, the epoxidized polyol ester molecules, especially epoxidized sucrose ester molecules, can interact more extensively, leading to a higher bulk viscosity and higher density. Since even in the "fully substituted" sucrose esters there are some residual hydroxyl groups, hydrogen bonding may also occur between the molecules. Indeed, the bulk viscosity and density of the partially substituted epoxidized sucrose ester is higher than its fully substituted counterpart, due to the additional hydrogen bonding. This increase in polarity is also reflected in a more well-defined glassy state as is indicated by the sharp glass transitions observed.

The epoxidation of sucrose esters of ethylenically unsaturated vegetable oil fatty acids has resulted in unique biobased resins having a high concentration of epoxy groups. As has been seen, functionalities of 8 to 15 epoxide groups per molecule may be achieved, depending on the composition of the fatty acid used and the degree of substitution of the fatty acids on the sucrose moiety. This is substantially higher than what can be achieved through epoxidation of triglycerides which range from about 4 for epoxidized soybean oil up to 6 for epoxidized linseed oil.

The high epoxide functionality of these resins coupled with the rigidity of a polyol having at least 4 hydroxyl groups per molecule, such as sucrose, has significant implications for the use of these resins and their derivatives in applications such as thermosetting materials. With the epoxidized polyol esters of fatty acids, EPEFA's, cross-linked materials having an outstanding combination of properties can be achieved.

Another embodiment of the invention relates to a resin which is a derivative of an EPEFA from the ring-opening reaction of the EPEFA with an ethylenically unsaturated acid, acrylated EPEFA's, and the use of such acrylated derivatives in coating compositions. The acrylation of an EPEFA may be done by a ring-opening reaction of the epoxy rings of the EPEFA with an ethylenically unsaturated acid monomer by methods known the art. Acid-epoxy catalyst is used to increase the rate of reaction. See Bajpai, et al., *Pigment & Resin Technology* 2004, 33, 160. Ethylenically unsaturated acid monomers such as acrylic acid, methacrylic acid, crotonic acid, and the like, and mixtures thereof, may be used. The acrylate groups in the acrylated EPEFA molecules (AEPFA's) functionalize the molecules to participate in free-radical polymerization in a coating composition. Ethylenically unsaturated diacids such as maleic acid, fumaric acid, and itaconic acid may also be used, alone, in mixtures, and in combination with ethylenically unsaturated acid monomers such as those just discussed, to introduce unsaturation and additional acid functionality.

The extent of reaction of the epoxy groups in the EPEFA with ethylenically unsaturated acids may be varied by varying the amount of ethylenically unsaturated acid used in the reaction. For example as little as 10% or less of the epoxy groups may be reacted up to as much as 100% of the epoxy groups, resulting in resins having varying degrees of ethylenically unsaturated functionality. As is known in the art, numerous catalysts can be used to catalyze the acid-epoxy reaction and are reviewed in Blank, et al., *J. Coat. Tech.*, 2002, 74, 33-41. Bases known to catalyze acid-epoxy reactions, such as 1,8-diazabicyclo[5.4.0]undec-7-ene (DBU), triethyl amine, pyridine, potassium hydroxide and the like may be used. Quaternary ammonium and quaternary phosphonium compounds can also be used to catalyze the reaction. In addition salts and chelates of metals such as aluminum, chromium, zirconium, or zinc may also be used. Catalysts AMC-2 and ATC-3 available from AMPAC Fine Chemicals are chelates of chromium and effective catalyst for acid-epoxy reactions.

In a further embodiment of the invention, an EPEFA may undergo a ring-opening reaction with an organic acid in acid-epoxy reaction, as is known in the art, to introduce hydroxyl functionality and form the corresponding EPEFA polyol. Introducing hydroxyl functionality at an epoxy group using base-catalyzed acid-epoxy reactions is known in the art. Organic acids which may be used include, for example, acetic acid, propionic acid, butyric acid, isobutyric acid, 2-ethylhexanoic acid, and mixtures thereof. Small, $C_1$-$C_{12}$, organic acids such as these are generally preferred but others may also be used. As discussed above, a number of catalysts can be used to catalyze an acid-epoxy reaction and are reviewed in Blank, et al., *J. Coat. Tech.*, 2002, 74, 33-41. Bases known to catalyze acid-epoxy reactions, such as 1,8-diazabicyclo[5.4.0]undec-7-ene (DBU), triethyl amine, pyridine, potassium hydroxide and the like may be used. Quaternary ammonium and quaternary phosphonium compounds can also be used to catalyze the reaction. In addition salts and chelates of metals such as aluminum, chromium, zirconium, or zinc may also be used. Catalysts AMC-2 and ATC-3 available from AMPAC Fine Chemicals are chelates of chromium and effective catalyst for acid-epoxy reactions.

The extent of reaction of the epoxy groups in the EPEFA with organic acids may be varied by varying the amount of organic acid used in the reaction. For example, as little as 10% or less of the epoxy groups may be reacted up to as much as 100% of the epoxy groups, resulting in polyols having varying degrees of hydroxyl functionality.

In a further embodiment of the invention, an EPEFA may undergo a ring-opening reaction with an organic alcohol to introduce hydroxyl functionality and form the corresponding EPEFA polyol. Organic alcohols which may be used include methanol, ethanol, n-propanol, n-butanol, isopropanol, isobutanol, 2-ethyl-1-hexanol, and the like as well as mixtures thereof. The resulting EPEFA polyol may be reacted with a polyisocyanate to form a thermoset polyurethane coating in the same way as conventional polyols known in the art.

The extent of reaction of the epoxy groups in the EPEFA with alcohol may be varied by varying the amount of alcohol used in the reaction. For example, as little as 10% or less of the epoxy groups may be reacted up to as much as 100% of the epoxy groups, resulting in polyols having varying degrees of hydroxyl functionality.

The resulting EPEFA polyol may be reacted with a polyisocyanate to form a thermoset polyurethane coating in the same way as conventional polyols known in the art. Any compound having two or more isocyanate groups can be used as a crosslinker. Aromatic, aliphatic, or cycloaliphatic isocyanates are suitable. Examples of isocyanates which can be used for crosslinking the polyols are hexamethylene diisocyanate, isophorone diisocyanate, toluene diisocyanate, methylene diphenyl diisocyanate, meta-tetramethylxylylene diisocyanate and the like. Adducts or oligomers of the diisocyanates are also suitable such as polymeric methylene diphenyl diisocyanate or the biuret or isocyanurate trimer resins of hexamethylene diisocyanate or isophorone diisocyanate. Adduct polyisocyanate resins can be synthesized by reacting a polyol with a diisocyanate such that unreacted isocyanate groups remain. For example, one mole of trimethyolopropane can be reacted with three moles of isophorone diisocyanate to yield an isocyanate functional resin.

Catalysts known in the art may be used to increase the curing speed of a polyol with a polyisocyanate to form polyurethane. Salts of metals such as tin, bismuth, zinc and zirconium may be used. For example, dibutyl tin dilaurate is a highly effective catalyst for polyurethane formation. Tertiary amines may also be used as a catalyst for urethane formation as is known in the art, such as for example, triethyl amine, DABCO [1,4-diazabicyclo[2.2.2]octane], and the like.

Another embodiment of the invention relates to epoxy-anhydride curing compositions comprising an EPEFA (discussed above), an acid anhydride, and a curing catalyst, such as a tertiary amine catalyst known in the art. In this embodiment, the EPEFA's of the invention used as the epoxy-functional molecule in an epoxy-anhydride curing composition.

Any acid anhydride, such as those used in coatings applications, may be used to prepare an epoxy-anhydride coating composition of the invention. Examples of acid anhydrides which may be used include, but are not limited to, succinic anhydride, maleic anhydride, 4-Methyl-1,2-cyclohexanedicarboxylic anhydride (MCHDA), dodecynyl succinic anhydride, phthalic anhydride (PA), tetrahydrophthalic anhydride (THPA), hexahydrophthalic anhydride (HHPA), methyl tetrahydrophthalic anhydride (Me-THPA), methyl hexahydrophthalic anhydride (Me-HHPA), trialkyl tetrahydrophthalic anhydride (TATHPA), trimellitic anhydride, chlorendic anhydride, nadic methyl anhydride (methylbicyclo[2.2.1]hept-5-ene-2,3-dicarboxylic anhydride), pyromellitic dianhydride, benzophenone tetracarboxylic dianhydride and mixtures thereof. Preferred are those anhydrides which are liquid and miscible with the EPEFA resins.

Tertiary amine catalysts known in the art may be used in the coating compositions of the invention. Tertiary amine catalysts include at least one tertiary nitrogen atom in a ring system. Examples of tertiary amine catalysts include but are not limited to as 1,8-diazabicyclo[5.4.0]undec-7-ene (DBU), 1,4-diazabicyclo[2.2.2]octane (DABCO), 4-(dimethylamino)pyridine (DMAP), 7-methyl-1.5.7-triazabicyclo[4.4.0]dec-5-ene (MTBD), quinuclidine, pyrrocoline and similar materials.

The ratio of epoxy equivalents in the EPEFA to anhydride equivalents can be varied in order to vary the crosslink density and the properties of the thermoset.

In the examples below, epoxidized sucrose esters fatty acids, ESEFAs, derived from different vegetable oils (i.e. linseed, safflower, and soybean) and different substitution of sucrose esters of fatty acids, SEFAs, (i.e. sucrose soyate B6) were used to formulate epoxy-anhydride curing systems. 4-Methyl-1,2-cyclohexanedicarboxylic anhydride (MCHDA) was used as the anhydride, and 1,8-diazabicyclo [5.4.0]undec-7-ene (DBU) was used as a specified tertiary amine catalyst. A commercial product, Vikoflex 7170 epoxidized soybean oil (ESO), was used as the control to demonstrate the innovative concept of using ESEFAs in this study. By comparing with the control, the epoxy-anhydride curing based on the utilization of ESEFAs as the epoxy compounds proved to be very impressive.

Figure 3:
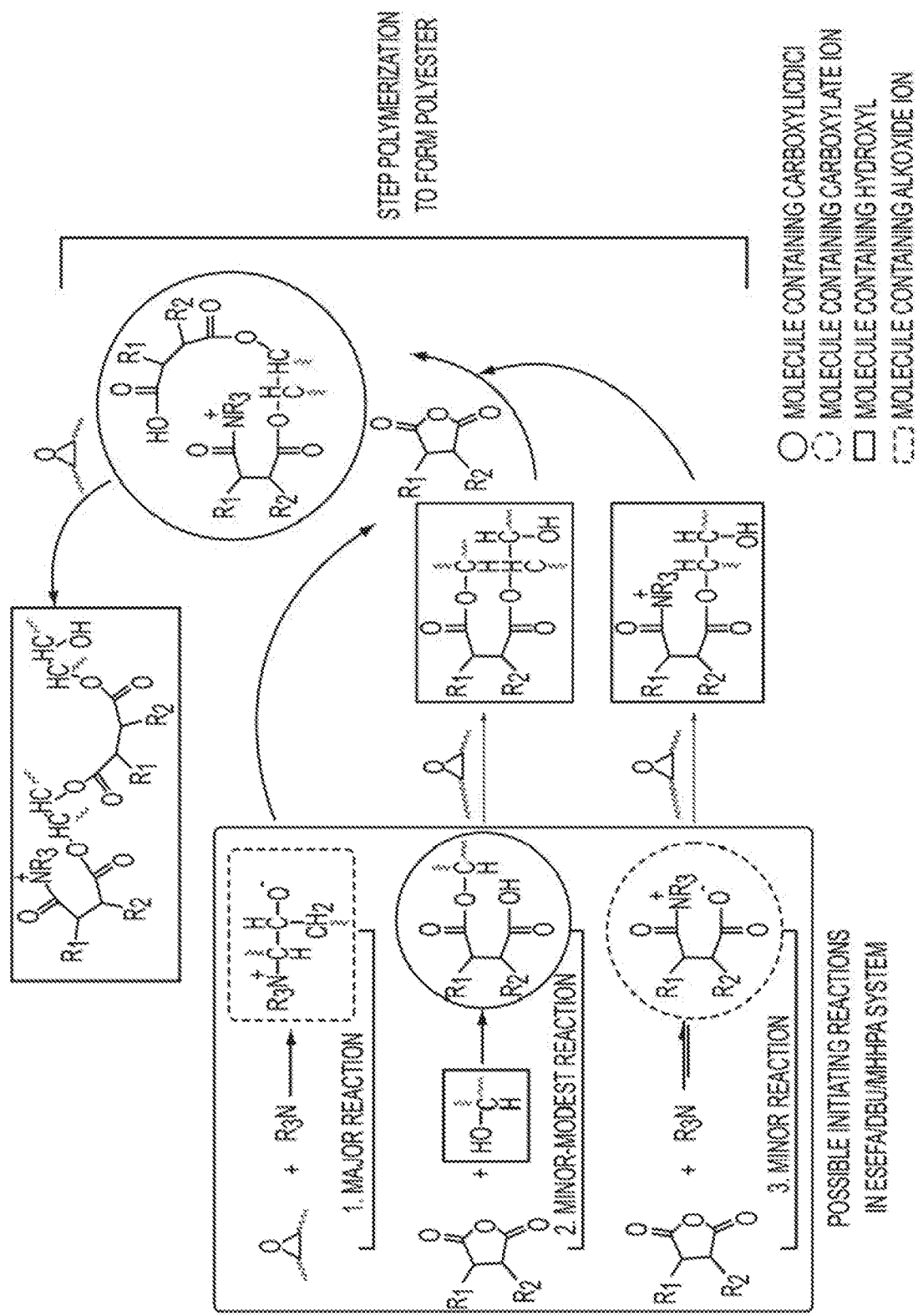
FIG. 3 depicts an exemplary epoxy-anhydride curing reaction.

FIG. 3 shows the main reactions that take place on curing ESEFA-MCHDA in the presence of amidine catalyst and trace hydroxyls. There are two reactions to initiate the polyester network formation: (a) DBU reacts with anhydride to create carboxylate; (b) hydroxyl reacts with anhydride to create carboxylic acid. In FIG. 3, R represents the organic moieties on the tertiary amine catalyst, $R_3N$, such as those on the tertiary amines described above. $R_1$ and $R_2$ represent the organic moieties on the acid anhydride, such as those discussed above.

A further embodiment of the invention involves the cationic polymerization of the epoxy groups in the EPEFA resins. Coating formulations can be prepared by mixing the epoxy resins with a photoinitiator, and optionally, a diluent resin.

It has been found that cationic photopolymerization of the epoxidized high functional resins yields films having greater hardness than those made from epoxidizied vegetable oils. In addition, surprisingly, the crosslinking reaction occurs at a faster rate for the highly functional epoxy resins than epoxidized vegetable oils.

Diluent resins can be low molecular weight epoxy resins such as the diglycidyl ether resins of bisphenol-A, cycloaliphatic epoxy resins, monofunctional epoxy resins, and the like. Oxetane-based compounds such as 3-hydroxymethyl, 3-ethyl oxetane, bis{[1-ethyl(3-oxetanyl)]methyl}ether, and the like, can also be used as diluent resins.

Hydroxy functional compounds can also serve as diluent resins. These can include alcohols such as butanol, 2-ethyl hexanol, 1,4-cyclohexanedimethanol, 1,3-cyclohexanedimethanol and the like. Polymeric polyols can also be used as diluents. These can be polyether polyols such as polyethylene glycols, polypropylene glycols, polytetramethylene diols. Polyester polyols such as polycaprolactones can also be incorporated as diluents.

Examples of photoinitiators used for effecting the cationic photopolymerization of the coating mixture are the diaryliodonium salts, triarylsulfonium salts, diaryliodosonium salts, dialkyl phenylsulfonium salts, dialkyl(hydroxydialkylphenyl)-sulfonium salts and ferrocenium salts.

A further embodiment of the invention involves the free radical curing of the acrylated EPEFA resins. Formulations may be prepared by mixing the acrylated EPESA resin with an optional diluent, an optional solvent, and a photoinitiator.

When a coating composition contains an acrylated EPEFA, diluents the diluents may be ones used in free radical or vinyl polymerizations such as but not limited to, isodecyl acrylate, 2-hydroxyethyl acrylate, butyl acrylate, 2-ethylhexyl acrylate, 1,6-hexanediol diacrylate, trimethylolpropane triacrylate, pentaerythritol tetraacrylate, ethoxylated trimethylolpropane triacrylate, and acrylated epoxidized soybean oil.

For curing of the acrylated EPEFA compounds and formulations, a free radical photoinitiator is needed. Suitable free radical photoinitiators include cleavage or Norrish I type photoinitiators or Norrish type II photoinitiators known in the art. Examples of Norrish type I photoinitiators are 2-hydroxy-2-methyl-1-phenyl-1-propanone, 2,2-diethoxyacetophenone, benzildimethylketal, 1-hydroxycyclohexylphenyl-ketone, 2,2'dimethoxy-2-phenylacetophenone and the like, Examples of Norrish type II photoinitiators are benzophenone, benzio, xanthone, thioxanthone, and the like, combined with synergists such as triethanolamine, triethylamine, dimethylethanol amine, and the like.

The invention also relates to the use of a coating composition which may be coated onto a substrate and cured using techniques known in the art. The substrate can be any common substrate such as paper, polyester films such as polyethylene and polypropylene, metals such as aluminum and steel, glass, urethane elastomers, primed (painted) substrates, and the like. The coating composition of the invention may be cured thermally or photochemically, e.g. UV or electron beam cure.

Pigments and other additives known in the art to control coating rheology and surface properties can also be incorporated. For example a coating composition of the invention may further contain coating additives. Such coating additives include, but are not limited to, one or more leveling, rheology, and flow control agents such as silicones, fluorocarbons or cellulosics; extenders; reactive coalescing aids such as those described in U.S. Pat. No. 5,349,026, incorporated herein by reference; plasticizers; flatting agents; pigment wetting and dispersing agents and surfactants; ultraviolet (UV) absorbers; UV light stabilizers; tinting pigments; colorants; defoaming and antifoaming agents; anti-settling, anti-sag and bodying agents; anti-skinning agents; anti-flooding and anti-floating agents; biocides, fungicides and mildewcides; corrosion inhibitors; thickening agents; or coalescing agents. Specific examples of such additives can be found in Raw Materials Index, published by the National Paint & Coatings Association, 1500 Rhode Island Avenue, N.W., Washington, D.C. 20005. Further examples of such additives may be found in U.S. Pat. No. 5,371,148, incorporated herein by reference.

Solvents may also be added to the coating formulation in order to reduce the viscosity. Hydrocarbon, ester, ketone, ether, ether-ester, alcohol, or ether-alcohol type solvents may be used individually or in mixtures. Examples of solvents can include, but are not limited to benzene, toluene, xylene, aromatic 100, aromatic 150, acetone, methylethyl ketone, methyl amyl ketone, butyl acetate, t-butyl acetate, tetrahydrofuran, diethyl ether, ethylethoxy propionate, isopropanol, butanol, butoxyethanol, and so on.

EXAMPLES

Methods:

The following methods are used in the examples for the characterization of the compounds synthesized and materials prepared.

Molecular weight was determined by gel permeation chromatography (GPC) using a Waters 2410 system equipped with refractive index detector. Polystyrene standards were used for calibration. A 1.5% sample solution in THF using a flow rate of 1 ml/min was used.

MALDI-TOF (matrix assisted laser desorption ionization-time of flight) mass spectra were recorded on a Bruker Ultraflex II spectrometer equipped with a 1.85 m linear flight tube and a Smart beam laser. All mass spectra were obtained in positive ion and linear mode. Samples were dissolved in THF (1 mg/mL), and α-cyano-4-hydroxycinnamic acid (10 mg/mL in THF) was used as matrix, and trifluoroacetic acid (0.1 wt % in water) was used as the dopant. A mixture of 10 μL of the matrix solution, 2 μL of the dopant, and 2 μL of the polymer solution was prepared and a 2 μL sample was spotted on the target plate. All data were processed using Flex analysis and PolyTools software package.

FTIR measurements were done by a Thermo Nicolet 8700 FTIR spectrometer. Spectra acquisitions were based on 32 scans with data spacing of 4.0 $cm^{-1}$ in the range of 4000-500 $cm^{-1}$.

NMR measurements were done at 23° C. using a JOEL-ECA (400 MHz) NMR spectrometer with an auto sampler accessory. All measurements were made using $CDCl_3$ as solvent. The data was processed using the Delta software package.

The bulk viscosities of samples were measured using a Brookfield Viscometer (DV-II+ Pro) at 21° C.

Intrinsic viscosity [η] of the materials was measured in THF with a Cannon-Fenske viscometer (size 50) at 25° C. The concentration of solution was 3.7-9.0 g/100 mL, and the relative viscosity $η_r$ was controlled in the good range of 1.1-1.6. The extrapolations of reduced viscosity and inherent viscosity were averaged to yield the intrinsic viscosity for each sample.

The densities of samples were measured using a BYK-Gardner Weight Per Gallon Cup at 25° C., referring to ASTM D 1475. The Midget Cup having a capacity of 8.32 grams of water at 25° C. was used. The net weight of the fluid sample in grams equals the sample's density in pounds per U.S. gallon, which is converted into grams/m L.

A DSC Q1000 from TA Instruments (New Castle, Del.) with an auto sampler was used for glass transition temperature ($T_g$) determination. Samples were subjected to a heat-cool-heat cycle from −90 to +100° C. by ramping at 10°

C./min for both heating and cooling cycles. The second heating cycle was used to characterize the samples.

Iodine values were determined according to ASTM D 5768.

Epoxide equivalent weight (EEW, g/eq.) of the epoxy products was determined by epoxy titration according to ASTM D 1652.

Acid value is measured according to ASTM D 465.

Photo-DSC experiments were obtained using a Q1000 Differential Scanning calorimeter (TA Instruments) equipped with a photo-calorimetery accessory (PCA). The experiment was run under 25° C. and with 1 min exposure time. The intensity of the UV light source was 50 mW/cm$^2$. The Photo-DSC was followed by a regular DSC scan with temperature range of −50° C. to 200° C. at a ramp of 10° C./min. A heating, cooling and heating cycle were monitored.

Impact test were measured according to ASTM D 2794 using a BYK-Gardner Heavy Duty Impact Tester Model IG-1120, with a 1.8 kg (4 lb) mass and 1.27 cm (0.5 in) diameter round-nose punch.

A BYK-Gardner pendulum hardness tester was used to measure the Konig pendulum hardness of the cured film in accordance with ASTM D 4366.

MEK double rubs of the cured film was done in accordance with ASTM D 5402.

The film thickness was measured with a Byko-test 8500.

König pendulum hardness and pencil hardness were measured using ASTM D 4366-95 and ASTM D 3363-00, respectively.

The adhesion of coatings on steel substrate was evaluated using crosshatch adhesion ASTM D 3359-97.

Mandrel bend test was carried out based on ASTM D 522, and the results were reported as the elongation range of coating at cracking.

For tensile testing, die-cut specimens were prepared from the thin films (0.10-0.16 mm) and thick samples (1.6-2.0 mm) according to ASTM D 638. The tensile tests were carried out at 25° C. using Instron 5542 (Norwood, Mass.). The grip separation distance of the tensile testing was 25.4 mm, and the effective gauge length was 20.4 mm. The crosshead speed was 0.1% elongation/sec. (0.0204 mm/sec.). The tensile properties of each sample were reported as the average of 5 measurements taken at different specimens and the uncertainty was the standard deviation.

Dynamic mechanical properties of thermosetting films were measured in tension mode using Q800 DMA from TA Instruments (New Castle, Del.). Rectangular specimens with dimensions of 20 mm length, 5 mm width, and 0.10-0.16 mm thickness were prepared. The measurements were performed from −110 to 200° C. at a heating rate of 5° C./min and frequency of 1 Hz. The glass transition temperature ($T_g$) was determined as the temperature at the maximum of tan δ vs. temperature curve. The storage modulus (E') in the rubbery plateau region was determined at generally 60° C. above the glass transition temperature. The crosslink density ($v_e$) of thermoset was calculated using E' in the rubbery plateau region by the following equation, derived from the theory of rubber elasticity: where E' is the storage modulus of the thermoset in the rubbery plateau region at $T_g$+60° C., R is the gas constant, and T is the absolute temperature.

$$E'=3v_e RT$$

Example 1. Preparation of Epoxidized Sucrose Esters (ESE) of Fatty Acids 1.1 Starting Materials:

The sucrose esters of fatty acids (SEFA's) were received from Procter & Gamble Chemicals (Cincinnati, Ohio). Acetic acid (ACS reagent, ≥99.7%), diethyl ether (ACS reagent, 99.0%), hydrogen peroxide (50 wt % solution in water), Amberlite IR-120H ion-exchange resin, sodium carbonate (ACS reagent), and anhydrous magnesium sulfate (reagent grade, ≥97%) were purchased from Sigma-Aldrich, Inc. (St. Louis, Mo.). All materials were used as received without further purification.

1.2 Method:

Four SEFOSE sucrose esters derived from different vegetable oils (Table 1) were epoxidized using peracetic acid generated in situ from hydrogen peroxide and acetic acid, in the presence of Amberlite IR 120H as catalyst using the method described below for the epoxidation of sucrose linseedate. Table 3 lists the sucrose esters of fatty acids. The epoxidation reactions were carried out in a 500 mL four-neck flask, equipped with a mechanical stirrer, a nitrogen inlet, a thermocouple and an addition funnel.

TABLE 3

Sucrose Esters of Fatty Acids Used.

| Name Full | Abbreviated | The type of plant oil | Average degree of substitution | Iodine value, $IV_0$ | Viscosity (mPa · s) |
| --- | --- | --- | --- | --- | --- |
| Sucrose linseedate | SL | Linseed | 7.7 | 177 | 236 |
| Sucrose safflowerate | SSF | Safflower | 7.7 | 133 | 393 |
| Sucrose soyate | SS | Soybean | 7.7 | 117 | 425 |
| Sucrose soyate B6 | SSB6 | Soybean | 6.0 | 115 | 890 |

Sucrose linseedate (170 g, 0.07 mol) containing 1.17 mol double bonds, acetic acid (35.1 g, 0.585 mol), and Amberite 120H (34 g, 20 wt % of sucrose linseedate) were charged to the reaction flask. The molar ratio of acetic acid:hydrogen peroxide ($H_2O_2$):double bond was controlled as 0.5:2:1. The mixture was rapidly stirred and nitrogen purged, and the temperature was raised to 55° C. Hydrogen peroxide (50 wt % aqueous solution, 160 g, 2.35 mol) was added dropwise using an addition funnel at a rate such that the reaction temperature was controlled in the range of 55-65° C. After the completion of the hydrogen peroxide addition, the reaction was stirred at 60° C. for 30 minutes. The product was transferred into a separatory funnel and allowed to cool to room temperature. After the aqueous layer was drained, the organic layer was diluted by 300 mL diethylene ether and washed with water five times. A saturated sodium carbonate/water solution was used as the last wash to completely remove the acetic acid. The organic layer was transferred into a beaker and dried with anhydrous magnesium sulfate overnight. The hydrated magnesium sulfate was removed by filtration, and diethylene ether was removed by rotavapping. Finally, a transparent viscous liquid was obtained as the epoxidized sucrose linseedate. The other SEFAs (sucrose safflowerate, sucrose soyate, and sucrose soyate B6) were epoxidized and purified using the same process. The recovered yields were all about 97 percent.

1.3 Results:

The SEFOSE sucrose esters used in this example are initially amber liquids, and sucrose linseedate and sucrose soyate B6 are darker brownish-yellow. The abbreviated name of the epoxidized sucrose ester is defined by adding an E in front of the abbreviated name of the corresponding sucrose ester. The four epoxidized sucrose esters synthesized by the above method are: epoxidized sucrose linseedate (ESL), epoxidized sucrose safflowerate (ESSF), epoxidized sucrose soyate (ESS), and epoxidized sucrose soyate B6 (ESSB6). Due to the epoxidization of double bonds and the bleaching action of the peroxide, the epoxidized sucrose esters are all colorless. It is commonly observed that epoxidized vegetable oils tend to become hazy on standing due to crystallization during storage. However, the epoxidized sucrose esters remain transparent during storage with no haze formation observed after several months.

Characterization of the products using proton and carbon 13 NMR and FTIR all indicated that the expected products had been successfully synthesized.

The conversion of double bonds, epoxide equivalent weights, and epoxide functionalities for the ESE resins synthesized are shown in Table 4. The iodine value (IV) can be used to determine the conversion of double bonds to epoxides using equation (1), where $IV_0$ is the iodine value of the starting sucrose ester, and $IV_f$ is the iodine value of the epoxy product. The conversion of double bonds to epoxy groups for all resins was greater than 99 percent.

$$\% \text{ Conversion} = 100 \times \frac{IV_0 - IV_f}{IV_0} \quad (1)$$

The epoxide functionality (EF) of the epoxy products can be estimated using the epoxide equivalent weight (EEW) and MALDI-TOF molecular weight values using equation (2), where $W_i$ is the average MW of epoxidized sucrose ester with the degree of substitution i. For fully substituted epoxidized sucrose esters, i equals 8. For epoxidized sucrose soyate B6, i equals 6.

$$EF = \frac{W_i}{EEW} \quad (2)$$

The epoxide functionality is higher for those sucrose ester resins having higher amounts of double bonds, as would be expected. It is lowest for the partially substituted sucrose soyate resin, SSB6, since only six of the eight available hydroxyls on sucrose are substituted with the ethylenically unsaturated soya fatty acid. The epoxide functionality is quite high for these resins; much higher than can be achieved through epoxidation of triglyceride oils such as soybean oil, where the epoxy functionality would be around 4.4.

TABLE 4

Properties of the epoxidized sucrose esters of fatty acids (ESEFAs).

| Epoxy product | $IV_f$ | % Conversion | $W_i$ (g/mol) | EEW (g/eq.) | Epoxide functionality |
|---|---|---|---|---|---|
| ESL | 0.16 | 99.9 | 2,701 | 180 | 15.0 |
| ESSF | 0.32 | 99.8 | 2,651 | 228 | 11.6 |
| ESS | 0.44 | 99.6 | 2,623 | 248 | 10.6 |
| ESSB6 | 0.73 | 99.4 | 2,048 | 256 | 8.0 |

Example 2. UV-Curable Coating Formulations of Epoxidized Sucrose Esters of Fatty Acids 2.1 Materials and Methods:

The epoxidized sucrose linseedate (ESL), epoxidized sucrose safflowerate (ESSf) and epoxidized sucrose soyate (ESSy) were synthesized following the method in Example 1. UVR 6110, 3,4-epoxycyclohexylmethyl-3,4-epoxyhexane carboxylate, UVI 6974, a mixture of triarylsulfonium hexafluoroantimonate salts were obtained from Dow Chemical Company, USA. Oxt-101, 3-ethyl-3-hydroxymethyl oxetane (TMPO) was supplied by Togoasei America Inc. Epoxidized soybean oil (ESO) was procured from Arkema, USA. The properties of ESL, ESSy, ESSy and ESO are shown in Table 5.

TABLE 5

Viscosity and Epoxy Equivalent Weight of ESEs and ESO

| Sample | Epoxy Equivalent Weight (g/mole) | Epoxy groups/mole | Viscosity (mPa · s) |
|---|---|---|---|
| ESL | 183.31 | 14.18 | 8000 |
| ESSf | 229.56 | 11.33 | 5100 |
| ESSy | 252.19 | 10.31 | 2190 |
| ESO | 243.52 | 4.4 | 972 |

2.2 Coating Formulation:

The coating formulations are listed in Table 6. All formulations contained a cationic photoinitiator (UVI 6974) and a reactive diluent, Oxt-101. Formulations A-D contain the ESEs and ESO as the primary resins while formulations E-H contain a mixture of ESE/ESO and cycloaliphatic diepoxide UVR 6110. The coating formulations were mixed thoroughly in a homogenizer. The compatibility of the coating solutions are also shown in Table 4. UV-cured coating samples were obtained by passing 3 mil wet films on bare steel panels once (10 s) through a UV beam using a Fusion Cure System. The intensity was measured by UV Power Puck II as 1400 mW/cm².

TABLE 6

Coating Formulations

| Components (wt %) | Set I | | | | Set II | | | |
|---|---|---|---|---|---|---|---|---|
| | A | B | C | D | E | F | G | H |
| ESL | — | 57.9 | — | — | — | 51.5 | — | — |
| ESSf | 57.9 | — | — | — | 51.5 | — | — | — |
| ESSy | — | — | 57.9 | — | — | — | 51.5 | — |
| ESO | — | — | — | 57.9 | — | — | — | 51.5 |
| UVR 6110 | — | — | — | — | 6.4 | 6.4 | 6.4 | 6.4 |
| Oxt-101 | 38.6 | 38.6 | 38.6 | 38.6 | 38.6 | 38.6 | 38.6 | 38.6 |
| UVI 6974 | 3.5 | 3.5 | 3.5 | 3.5 | 3.5 | 3.5 | 3.5 | 3.5 |
| Solubility | Clear | Clear | Clear | Clear | Clear | Clear | Clear | Hazy |

Figure 4:
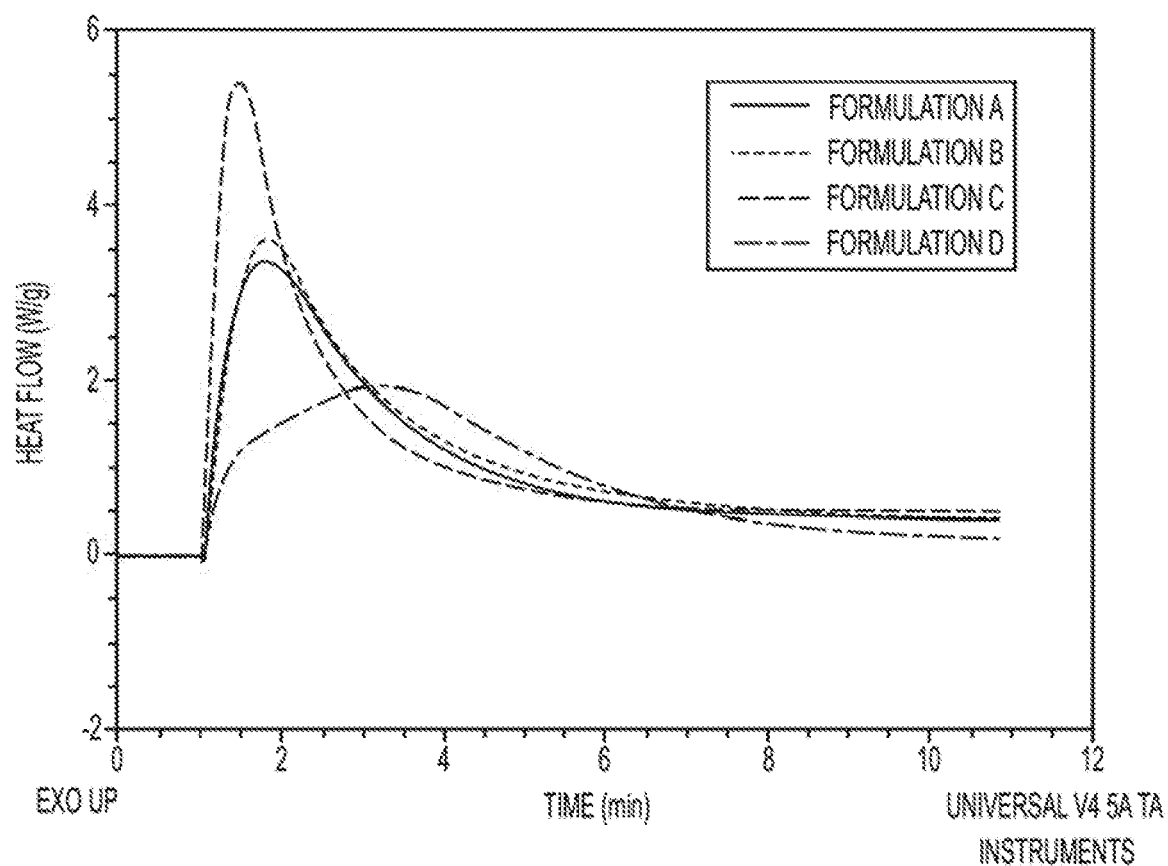
FIG. 4 depicts a Photo-DSC thermogram of a coating formulation containing ESE/ESO (Set I) from Example 2.
Figure 5:
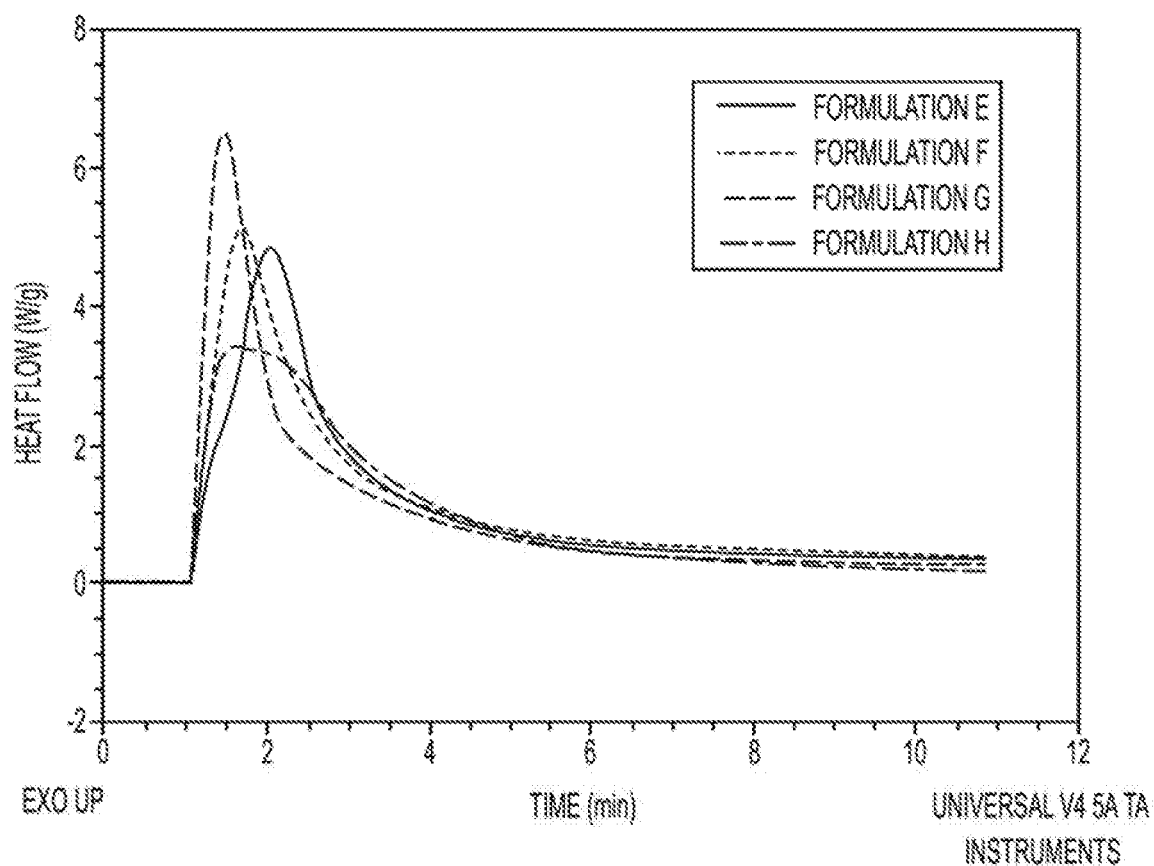
FIG. 5 depicts a Photo-DSC thermogram of a coating formulation containing ESE/ESO and UVR 6110 (Set II) from Example 2.

2.3 Results and Discussion:

Photo-DSC is an effective tool for the kinetic analysis of photo-polymerization (Chen, et al., *Polymer* 2002, 43, 5379; Zong, et al., J. Polym. Sci., Part A: Polym. Chem., 41 (2003), 3440; Cho, et al., *Polym. Test.* 2002, 21, 781; Cho J.; Kim E.; Kim H.; Hong J. Polym. Test. 2003, 22,633). The photo-DSC plot of the two set of formulations are shown in FIGS. 4 and 5. The exothermal peaks of the UV cured coatings in both FIGS. 4 and 5 show that formulations C and G, both containing ESSy, have a shorter induction time and shortest time for peak maximum indicating the fastest reacting system (Hong J. W.; Lee H. W., J. Korean Ind. & Eng. Chem. 1994, 5, 857). The ESL and ESSf have almost equal curing rate while ESO has the longest induction time and peak maximum. The higher curing rate of the ESSy can be attributed to the lesser steric strain of the epoxy groups to crosslink by ring opening reaction (Sangermano M.; Malucek G.; Priola A.; Manea M.; *Prog. Org. Coat.* 2006, 55, 225). A very fast initial curing process leads to surface shrinkage and also since vitrification starts early, further diffusion of monomers is prevented (Sangermano M.; Malucek G.; Priola A.; Manea M.; *Prog. Org. Coat.* 2006, 55, 225). This results in a post curing effect which can be shown by further thermal treatment.

The properties of the cured coatings are given in Table 7. All of the coatings based on epoxidized sucrose ester resins have higher $T_g$, hardness, and solvent resistance than the control based on ESO. The $T_g$ of the ESL system is expectedly the highest showing maximum network formation due to the high functionality of epoxy groups in the ESL resin. In strong contrast, the $T_g$ of the ESO system is below room temperature due to a lower amount of crosslinking due to lower epoxy groups per molecule. The ESL system also demonstrated the highest hardness and MEK double rubs showing an extensive crosslinked network. The ESO has low hardness and MEK double rubs showing that the coating has a lower crosslink density. In addition to the higher $T_g$ and good hardness, the coatings based on epoxidized sucrose esters also have good impact resistance. A consistent increase of the $T_g$, hardness, and solvent resistance of each system with the incorporation of UVR 6110 is also observed.

TABLE 7

Coating Properties

| Formulation | Glass Transition Temp. (° C.) | Film thickness (μm) | König Hardness (s) | Reverse Impact Resistance (in-lb) | MEK double rubs |
|---|---|---|---|---|---|
| A | 21.31 | 30.1 | 62 | 100 | 75 |
| B | 27.03 | 30.5 | 105 | 160 | 225 |
| C | 15.69 | 30.3 | 48 | 80 | 58 |
| D | −0.63 | 30.5 | 35 | 172 | 45 |
| E | 23.15 | 30.4 | 77 | 80 | 86 |
| F | 44.78 | 29.9 | 122 | 89 | 240 |
| G | 19.49 | 30.2 | 60 | 100 | 63 |
| H | 3.25 | 30.2 | 40 | 172 | 50 |

Example 3. Acrylation of an Epoxidized Sucrose Ester of a Fatty Acid 3.1 Materials:

Epoxidized sucrose soyate (ESSy) was prepared as in Example 1. Ampac Fine Chemicals provided AMC-2 Accelerator. Isodecyl acrylated (IDA) and 1,6-hexanediol diacrylate (HDODA) were obtained from Sartomer, while 2-hydroxyethyl acrylate (HEA) was purchased from Sigma-Aldrich. Darocur® 1173 photoinitiator was purchased from Ciba. Ebecryl 860, an acrylated epoxidized soybean oil, was obtained from Cytec.

3.2 Synthesis

The epoxy equivalent weight of the Epoxidized Sucrose Soyate (ESSy) was determined to be 248.79 g/mol. Acrylated resins were prepared having three different extents of acrylation (based on the number of epoxy groups). Table 8 contains the amount or reagents used for the acrylation of ESSy. AESSy is the fully acrylated resin, while PAESSy 50 indicates that 50 percent of the epoxy groups were acrylated and PAESSy indicates that 75 percent of the epoxy groups were acrylated.

TABLE 8

Acrylation of sucrose ester (SE) materials

| | ESSy | Oxirane Content | Extent of Acrylation | Acrylic Acid | Hydroquinone (2.5% by weight of oil + acrylic acid) | AMC-2 (1%) |
|---|---|---|---|---|---|---|
| PAESSy 50 | 50.0 g | 0.201 mol | 50% | 8.69 g 0.121 mol | 1.46 g | 0.581 g |
| PAESSy 75 | 50.0 g | 0.201 mol | 75% | 10.9 g 0.150 mol | 1.52 g | 0.609 g |
| AESSy | 50.0 g | 0.201 mol | 90% | 13.0 g 0.181 mol | 1.58 g | 0.630 g |

The required amount of ESSy, acrylic acid, 2.5% hydroquinone, and 1% AMC-2 were added in a three-necked 250 mL flask fitted with a condenser, thermometer, and a mechanical stirrer. Hydroquinone was added to prevent the homopolymerization of acrylate groups.[9] AMC-2 catalyst was used in the reaction. This catalyst is a mixture of 40-60% of phthalates ester and 40-60% of chromium 2-ethylhexanoate. The reaction mixture was heated to a temperature of 90° C. The extent of acrylation was monitored by measuring the acid value. The reaction was stopped when the acid value was in the range of 5-15.

3.3 Coating Formulations Containing Acrylated Epoxidized Resin

Coating formulations consisting of Acrylated Epoxidized Resin (either Ebecryl 860, PAESSy 50, PAESSy 75, or ASSy), solvents or diluents (20% by weight) to reduce viscosity, and Darocure 1173 (5% by weight) as the photoinitiator were prepared and hand-mixed. They were applied onto Q-panels (steel smooth finish, 0.020"×3"×6") and glass panels (at a thickness of about 40 μm using a film applicator. The coated panels were cured by exposing them to a UV lamp (Fusion LC6B Benchtop Conveyer with an F300 UV Lamp, intensity ~1180 mW/cm$^2$ by UV Power Puck® II from EIT Inc) for 20 sec.

The properties of the coatings are listed in Tables 9-12. Coatings based on acrylated epoxidized sucrose soyate (PAESSy 50, PAESSy 75, AESSy) have a high acrylate group functionality leading to coatings which are chemically resistive, hard, and inflexible. The hardness of the coatings from the acrylated epoxidized sucrose ester resins is greater than that of the acrylated epoxidized soybean oil based coatings. Overall, neither the degree of acrylation nor the type of diluents affected the coating properties significantly. The addition of diluents reduced viscosity by 90%, yet no changes in coating properties were observed.

TABLE 9

AESO (Ebercryl 860) Coating Properties

| | MEK | IDA | HEA | HDODA | HEA&HDODA |
|---|---|---|---|---|---|
| Film thickness (μm) | 51.3 | 42.8 | 47.5 | 37.5 | 39.6 |
| König Hardness (s) | 63 | 32 | 53 | 92 | 83 |
| Reverse Impact (inch-lb) | 40 | 20 | 28 | 28 | 48 |
| Pencil Hardness | HB | F | HB | F | HB |
| MEK double rub | >400 | 310 | >400 | >400 | >400 |
| Cross Hatch Adhesion | 0B | 0B | 0B | 0B | 0B |
| Mandrel Bend | >28% | >28% | >28% | <3% | ≈14% |

TABLE 10

PAESSy 50 Coating Properties

| | MEK | IDA | HEA | HDODA | HEA&HDODA |
|---|---|---|---|---|---|
| Film thickness (μm) | 42.5 | 47.5 | 42.1 | 39.8 | 36.3 |
| König Hardness (s) | 67 | 30 | 40 | 82 | 79 |
| Reverse Impact (inch-lb) | 14 | 20 | 20 | 12 | 16 |
| Pencil Hardness | B | 2B | 2B | HB | HB |
| MEK double rub | >400 | 298 | >400 | >400 | >400 |
| Cross Hatch Adhesion | 0B | 0B | 0B | 0B | 0B |
| Mandrel Bend | ≈20% | ≈25% | ≈20% | ≈4% | ≈14% |

TABLE 11

PAESSy 75 Coating Properties

| | MEK | IDA | HEA | HDODA | HEA&HDODA |
|---|---|---|---|---|---|
| Film thickness (μm) | 40.9 | 35.6 | 37.3 | 37.8 | 53.5 |
| König Hardness (s) | 100 | 75 | 108 | 109 | 103 |
| Reverse Impact (inch-lb) | 4 | 8 | 4 | 84 | 4 |
| Pencil Hardness | B | 2B | B | B | B |
| MEK double rub | >400 | 117 | >400 | >400 | >400 |
| Cross Hatch Adhesion | 0B | 0B | 0B | 0B | 0B |
| Mandrel Bend | <3% | ≈14% | ≈4% | <3% | <3% |

TABLE 12

AESSy Coating Properties

| | MEK | IDA | HEA | HDODA | HEA&HDODA |
|---|---|---|---|---|---|
| Film thickness (μm) | 42.3 | 40.8 | 36.4 | 56.8 | 37.6 |
| König Hardness (s) | 88 | 85 | 106 | 88 | 107 |
| Reverse Impact (inch-lb) | 4 | 4 | 4 | 4 | 4 |
| Pencil Hardness | B | HB | F | F | F |
| MEK double rub | >400 | 207 | >400 | >400 | >400 |
| Cross Hatch Adhesion | 0B | 0B | 0B | 0B | 0B |
| Mandrel Bend | <3% | <3% | <3% | <3% | <3% |

The high value of MEK double rub test suggested that the coatings were chemically resistive. All the coating formulations, except those containing IDA, had MEK double rubs above 400.

Based on Konig and pencil hardness, these coatings are considered to be hard. As the degree of acrylation increases, the coatings were harder. Impact test data shows that the coatings are brittle, indicating high crosslink density. Mandrel bend shows the flexibility of the film coatings. The lower cross-linking density of AESO and PAESSy 50 in formulations with the monoacrylate diluents is suggested to be the cause of flexibility of those coatings.

Example 4. Anhydride Curing of Epoxidized Sucrose Esters 4.1 Materials.

Sucrose esters of fatty acids (SEFAs) were provided by Procter & Gamble Chemicals (Cincinnati, Ohio). They were the starting materials to prepare epoxidized sucrose esters of fatty acids (ESEFA). There are four ESEFAs used in this study. They are ESL (epoxidized sucrose linseedate), ESSF (epoxidized sucrose safflowerate), ESS (epoxidized sucrose soyate), and ESSB6 (epoxidized sucrose soyate B6). The epoxidized sucrose ester resins were prepared as in Example 1. Vikoflex 7170 epoxidized soybean oil (ESO) was supplied by Arkema Inc. (Philadelphia, Pa.). 4-methyl-1,2-cyclohexanedicarboxylic anhydride (mixture of isomers, 98%), or hexahydro-4-methylphthalic anhydride (MHHPA), was purchased from Alfa Aesar (Heysham, England). 1,8-diazabicyclo[5.4.0]undec-7-ene (99.0% GC) (DBU) was purchased from Sigma-Aldrich Co. (St. Louis, Mo.).

4.2 Epoxy-Anhydride Formulation and Curing

The equivalent ratio of epoxides to anhydrides was 1:0.5 or 1:0.75. DBU was used at 1.5 wt % (based on the total weight of resins). The effects of stoichiometric ratio on thermosetting properties were studied using ESL and ESSB6. In ESL anhydride curing, the equivalent ratios of epoxides to anhydrides were used as 1:0.5, 1:0.4 and 1:0.3. In ESSB6 anhydride curing, the equivalent ratios of epoxides to anhydrides were used as 1:0.625, 1:0.5 and 1:0.4. As an example, the formulation of ESL anhydride curing in the equivalent ratio of epoxides to anhydrides of 1:0.5 is as follows: 10 g of ESL (3.70 mmoles) containing 54.64 mmoles epoxides, was mixed with 4.60 g of MHHPA (27.35 mmoles) containing 27.35 mmoles anhydride, in the presence of 0.219 g of DBU (1.44 mmoles).

ESEFA anhydride curing was done for 12 hours at 80° C., but ESO anhydride curing had to be done for 48 hours at 80° C. Coatings were cast on cleaned steel panels (QD panels from Q-panel) and glass panels using a draw-down bar with a gap of 8 mils. The thermosetting thin films (0.10-0.16 mm) on glass panels were carefully peeled off to make the specimens for DMA and tensile testing. Thick thermosetting samples were prepared by curing in Teflon molds, and their thicknesses were controlled in 1.6-2.0 mm.

4.3 Properties of the Cured Thermosets

The tensile properties of the cured thermosets are shown in Table 13. The modulus and tensile strength of the materials based on the epoxidized sucrose ester resins is significantly higher than that of the materials based on epoxidized soybean oil. The materials based on ESO are highly elastomeric, as indicated by the high value of elongation at break, while the materials based on the epoxidized sucrose soyate resins are much stiffer.

TABLE 13

The tensile properties of epoxy-anhydride thermosetting thin films in the equivalent ratio of epoxides to anhydrides of 1:0.5

| Epoxy compounds | Modulus (MPa) | Tensile strength (MPa) | Elongation at break (%) | Tensile toughness (J) × 10³ |
|---|---|---|---|---|
| ESL | 1395 ± 191 | 45.8 ± 5.4 | 5.7 ± 2.6 | 8.44 ± 3.5 |
| ESSF | 909 ± 179 | 31.5 ± 3.2 | 8.5 ± 2.7 | 11.5 ± 6.3 |
| ESS | 497 ± 38 | 20.3 ± 4.3 | 21.7 ± 7.8 | 29.4 ± 9.2 |
| ESSB6 | 1002 ± 52 | 35.1 ± 3.6 | 5.4 ± 0.7 | 9.1 ± 3.8 |
| ESO (Control) | 65 ± 10 | 10.2 ± 2.5 | 167 ± 19 | 97 ± 13.8 |

Different stoichiometric ratios of epoxy to anhydride can also be used to form the thermosetting materials. The properties of a series of materials are shown in Table 14 and show that varying the stoichiometric ratio can vary the properties of the materials.

TABLE 14

The tensile properties of epoxy-anhydride thermosetting thick samples in the equivalent ratio of epoxides to anhydrides of 1:0.75 and 1:0.5

| Epoxy compounds | Epoxide/ anhydride (equivalent ratio) | Modulus (MPa) | Tensile strength (MPa) | Elongation at break (%) |
|---|---|---|---|---|
| ESS | 1:0.5 | 170.8 ± 12.8 | 7.8 ± 0.4 | 11.0 ± 1.8 |
| ESS | 1:0.75 | 595.1 ± 8.2 | 21.8 ± 1.4 | 6.2 ± 1.0 |
| ESSB6 | 1:0.5 | 231.8 ± 40.5 | 8.9 ± 1.6 | 10.4 ± 2.2 |
| ESSB6 | 1:0.75 | 643.9 ± 26.1 | 19.6 ± 5.7 | 4.5 ± 0.7 |
| ESO (Control) | 1:0.5 | 5.0 ± 0.16 | 1.2 ± 0.1 | 27.9 ± 3.6 |
| ESO (Control) | 1:0.75 | 97.7 ± 28.7 | 6.0 ± 0.5 | 28.7 ± 5.6 |

The dynamic mechanical properties of the anhydride cured materials are given in Table 15. This data shows that the values of the glass transition temperatures obtained from the anhydride curing of the epoxidized sucrose ester resins is significantly higher than that obtained using ESO. In addition, the room temperature modulus also demonstrates that the ESE resins yield cured materials with significantly greater stiffness. The measured crosslink density (ve) in Table 13 also shows that the thermosets from the ESE resins is significantly higher than that from ESO due to the higher degree of epoxy functionality in the ESE resins.

TABLE 15

Dynamic mechanical properties and crosslink densities of epoxy-anhydride thermosets

| Epoxy compounds | Epoxide/ anhydride (equivalent ratio) | $T_g$ (° C.) | E' (MPa) at 20° C. | E' (MPa) at $T_g$ + 60° C. | $v_e$ (×10³ mol/mm³) |
|---|---|---|---|---|---|
| ESL | 1:0.5 | 103.7 | 1,500 | 20.7 | 1.84 |
| ESL | 1:0.4 | 78.5 | 619 | 9.5 | 0.85 |
| ESL | 1:0.3 | 46.9 | 141 | 6.6 | 0.59 |
| ESSF | 1:0.5 | 71.3 | 1,103 | 7.7 | 0.69 |
| ESS | 1:0.5 | 48.4 | 103 | 5.6 | 0.50 |
| ESSB6 | 1:0.5 | 79.6 | 368 | 13.8 | 1.23 |
| ESO (Control) | 1:0.5 | 24.8 | 36 | 3.1 | 0.28 |

Coatings were made from the anhydride curing of the ESE resins and the control ESO and the data is shown in Table 16. As can be seen, the hardness of the coatings based on ESE resins is significantly higher than the coatings based on ESO. Solvent resistance for the ESE coatings is also significantly better than ESO.

TABLE 16

The properties of epoxy-anhydride coatings

| Epoxy compounds | Epoxide/ anhydride (Eq. ratio) | Thickness (μm) | König pendulum hardness (sec.) | Pencil hardness (gouge) | Cross-hatch adhesion | MEK double rub resistance | Reverse impact (in-lb) | Mandrel bend (elongation-at-break) |
|---|---|---|---|---|---|---|---|---|
| ESL | 1:0.5 | 110 ± 7.0 | 183 | H | 4B | >400 | 28 | <2.5% |
| ESL | 1:0.4 | 120 ± 17.7 | 90 | F | 5B | >400 | >172 | >28% |
| ESL | 1:0.4 | 94.4 ± 5.4 | 47 | B | 5B | 330 | >172 | >28% |
| ESSF | 1:0.5 | 113 ± 3.3 | 118 | F | 5B | >400 | 32 | 4-4.5% |
| ESS | 1:0.5 | 102 ± 8.4 | 63 | 2B | 5B | >400 | 72 | >28% |
| ESSB6 | 1:0.625 | 99.8 ± 2.5 | 123 | HB | 3B | >400 | 100 | >28% |
| ESSB6 | 1:0.5 | 112 ± 4.5 | 115 | B | 5B | >400 | 80 | >28% |
| ESSB6 | 1:0.4 | 99.5 ± 4.4 | 39 | 2B | 2B | 320 | >172 | >28% |
| ESO (Control) | 1:0.5 | 108 ± 4.8 | 22 | <EE | 5B | 25 | >172 | >28% |

Example 5. Synthesis of Epoxidized Soyate Esters of Dipentaerythritol and Tripentaerythritol 5.1 Materials:

Sucrose esters of soybean oil fatty acids, sucrose soyate, were provided by Procter & Gamble Chemicals (Cincinnati, Ohio). Acetic acid (ACS reagent, ≥99.7%), diethyl ether (ACS reagent, ≥99.0%), hydrogen peroxide (50 wt % solution in water), Amberlite IR-120H ion-exchange resin, sodium carbonate (ACS reagent), and anhydrous magnesium sulfate (reagent grade, ≥97%) were purchased from Sigma-Aldrich, Inc. (St. Louis, Mo.).

Vikoflex 7170 epoxidized soybean oil was supplied by Arkema Inc. (Philadelphia, Pa.). RBD soybean oil was provided by Industrial Oils & Lubricants (Chicago, Ill.). BDH™ Methanol (ACS grade, 99.8%) was purchased from VWR International (West Chester, P.⁴). Potassium hydroxide (technical grade) was purchased from Mallinckrodt Baker, Inc. (Phillipsburg, N.J.). Dipentaerythritol (technical grade) and tripentaerythritol (technical grade) were purchased from Sigma-Aldrich, Inc. (St. Louis, Mo.). Dibutyltin oxide (98%) and dibutyltin dilaurate (95%) were purchased from Sigma-Aldrich, Inc. (St. Louis, Mo.). All materials were used as received without further purification.

5.2 Synthesis of Fatty Acid Methyl Ester:

The synthesis of fatty acid methyl ester was carried out in a 500 mL four-neck flask equipped with a mechanical stirrer, nitrogen inlet, thermocouple, and reflux condenser. 200 g of soybean oil (0.230 moles) was charged into the flask and was preheated to 65° C. with nitrogen purge. 9.3 g of potassium hydroxide (0.166 moles) was dissolved into 110.5 g of methanol (3.449 moles), and the solution was slowly charged into the flask to start the transesterification reaction. The methanol/oil molar ratio was 15:1, and the catalyst concentration was 3.2 wt % (based on the total weight of oil and methanol). The reaction temperature was kept at 65±1° C. with methanol refluxing. The reaction was allowed to run for 3 hours, and finally a transparent brownish red solution was obtained. After it was cooled down to room temperature, the solution was transferred into a separatory funnel. A large amount of distilled water was charged into the funnel, and the reaction mixture was separated into two phases. The upper phase consisted of methyl esters, and the lower phase contained the glycerol, monoglyceride, possible diglyceride, potassium hydroxide, and the excess of methanol. The upper methyl esters layer was successively purified with distilled water until the water layer was clear. The residual water inside of methyl esters was eliminated by treatment with anhydrous magnesium sulfate, followed by filtration. Finally, methyl esters were obtained as the light yellow liquid. Usually, the yield of this FAME synthesis was in the range of 65-70% due to the loss of monoglyceride in water.

5.3 Synthesis of Multi-Pentaerythritol Soyate:

The synthesis of multi-pentaerythritol soyate was carried out in a 250 mL four-neck flask equipped with a mechanical stirrer, nitrogen inlet, thermocouple, condenser, and Dean-Stark trap. The degree of fatty acid substitution on multi-pentaerythritol was controlled by the FAME/multi-pentaerythritol molar ratio. Herein, the synthesis of tripentaerythritol soyate with full substitution was demonstrated as an example. 25 g of tripentaerythritol (0.037 moles) and 157 g of FAME (0.537 moles) were charged into the flask and preheated to 225° C. with nitrogen purge. Dibutyltin dilaurate and dibutyltin oxide were used as the organotin catalyst, and they were individually added in 0.05 wt % based on the total weight of tripentaerythritol and FAME. As the byproduct of the transesterification, methanol was collected in the Dean-Stark trap. The reaction was allowed to run for 7 hours, and finally tripentaerythritol soyate was obtained as the yellow liquid resin.

5.4 Synthesis of Epoxidized Soyate Resins:

Epoxidation reactions were carried out in a 500 mL four-neck flask, equipped with a mechanical stirrer, nitrogen inlet, thermocouple and addition funnel. Soyate resins were epoxidized using peracetic acid generated in situ from hydrogen peroxide and acetic acid, in the presence of Amberlite IR 120H as catalyst. The molar ratio of acetic acid:hydrogen peroxide ($H_2O_2$):double bond was used in 0.5:2:1. The properties of the resins are shown in Table 17.

TABLE 17

Properties of resins before and after epoxidation

| Resin | Epoxidation | EEW (g/eq.) | Iodine value | Viscosity (mPa·s) | Density (g/cm³) at 25° C. | Intrinsic viscosity (100 ml/g), 25° C. in THF | Mn (g/mol) | GPC MW difference (g/mol) | PDI |
|---|---|---|---|---|---|---|---|---|---|
| Soybean oil | Cargill ™ | — | 136 | 79 | 0.920 | 1.10 | 1,290 | 29 | 1.10 |
| ESO | Vikoflex ™ 7170 | 231 | — | 588 | 0.996 | 2.36 | 1,319 | | 1.14 |
| Dipentaerythritol soyate (DPS) | Before | — | 124 | 341 | 0.939 | 2.92 | 2,353 | 130 | 1.26 |
| | After | 268 | 1.25 | 1,192 | 1.000 | 3.27 | 2,483 | | 1.28 |
| Tripentaerythritol soyate (TPS) | Before | — | 124 | 415 | 0.943 | 3.32 | 2,807 | −35 | 1.15 |
| | After | 261 | 1.36 | 1,368 | 1.001 | 3.58 | 2,772 | | 1.18 |
| Tripentaerythritol soyate B6 (TPS B6) | Before | — | 125 | 365 | 0.946 | 2.98 | 2,349 | 156 | 1.11 |
| | After | 270 | 1.05 | 1,824 | 1.011 | 3.21 | 2,505 | | 1.13 |
| Sucrose soyate (SS) | Before | — | 117 | 425 | 0.945 | 2.41 | 2,379 | 252 | 1.08 |
| | After | 248 | 0.44 | 2,160 | 1.017 | 3.15 | 2,631 | | 1.08 |
| Sucrose soyate B6 (SS B6) | Before | — | 115 | 890 | 0.965 | 1.83 | 2,204 | 274 | 1.09 |
| | After | 256 | 0.73 | 5,460 | 1.036 | 2.94 | 2,478 | | 1.20 |

Example 6. Coating Formulation and Properties

4-Methyl-1,2-cyclohexanedicarboxylic anhydride (mixture of isomers, 98%) (MHHPA) was purchased from Alfa Aesar (Heysham, England). Dodecenylsuccinic anhydride (mixture of isomers), and 1,8-diazabicyclo[5.4.0]undec-7-ene (≥99.0% GC) (DBU) were purchased from Sigma-Aldrich Inc. (St. Louis, Mo.). Coatings were formulated at a 1:0.5 ratio of epoxy to anhydride. Formulations were prepared as described in Example 4 and cured at 85° C. for 12 hours.

Properties of the coatings cured using MHHPA are shown in Table 18 and properties for coatings cured using DDSA are shown in Table 19. The properties vary over a broad range depending on the structure of the epoxy resins, the curing agent used and the stoichiometric ratio.

TABLE 18

Properties of epoxy-anhydride coatings using MHHPA hardener
(4-methyl-1,2-cyclohexanedicarboxylic anhydride)

| Epoxy | Epoxide/anhydride (molar ratio) | Thickness (μm) | Pendulum hardness, sec | Pencil hardness (gouged) | Cross-hatch adhesion | MEK double rubs | Impact (inch-lbs) | Mandrel Bending (elongation-at-break) |
|---|---|---|---|---|---|---|---|---|
| ESO | 1:0.5 | 108 ± 4.8 | 17 | <EE | 5B | 25 | >172 | >28% |
| EDPS | 1:0.5 | 70.2 ± 4.9 | 37 | EE | 5B | 55 | >172 | >28% |
| ETPS | 1:0.5 | 85.1 ± 5.1 | 24 | EE | 5B | 75 | >172 | >28% |
| ETPS_B6 | 1:0.5 | 93.6 ± 7.6 | 16 | 3B | 5B | 108 | 148 | >28% |
| ESS | 1:0.5 | 102 ± 8.4 | 63 | 2B | 5B | >400 | 72 | >28% |
| ESS_B6 | 1:0.5 | 112 ± 4.5 | 115 | B | 5B | >400 | 80 | >28% |

TABLE 19

Properties of epoxy-anhydride coatings using DDSA hardener (dodecenylsuccinic anhydride)

| Epoxy | Epoxide/anhydride (molar ratio) | Thickness (μm) | Pendulum hardness, sec | Pencil hardness (gouged) | Cross-hatch adhesion | MEK double rubs | Impact (inch-lbs) | Mandrel Bending (elongation-at-break) |
|---|---|---|---|---|---|---|---|---|
| ESO | 1:0.5 | 89.4 ± 7.5 | 40 | <EE | 3B | 87 | 160 | >28% |
|  | 1:0.75 | 79.3 ± 4.3 | 22 | <EE | 4B | 60 | >172 | >28% |
| EDPS | 1:0.5 | 84.9 ± 9.2 | 40 | 5B | 4B | 238 | 120 | >28% |
|  | 1:0.75 | 80.2 ± 8.3 | 17 | 2B | 5B | 164 | >172 | >28% |
| ETPS | 1:0.5 | 85.9 ± 10.7 | 22 | 4B | 5B | 115 | >172 | >28% |
|  | 1:0.75 | 96.6 ± 8.5 | 18 | 2B | 5B | 91 | >172 | >28% |
| ETPS_B6 | 1:0.5 | 102.2 ± 6.9 | 13 | 3B | 5B | 150 | 140 | >28% |
|  | 1:0.75 | 90.3 ± 9.3 | 34 | HB | 4B | 167 | 128 | >28% |
| ESS | 1:0.5 | 97.6 ± 10.2 | 22 | 2B | 5B | 300 | 140 | >28% |
|  | 1:0.75 | 93.4 ± 8.7 | 44 | B | 5B | >400 | >172 | >28% |
| ESSB6 | 1:0.5 | 97.2 ± 8.3 | 56 | F | 5B | 350 | 160 | >28% |
|  | 1:0.75 | 101.0 ± 7.4 | 92 | F | 5B | >400 | >172 | >28% |

Example 7. Polyols from Epoxidized Sucrose Soyate Resins and Polyurethane Coatings 7.1 Raw Materials Epoxidized sucrose soyate (ESS) and epoxidized sucrose soyate B6 (Ess B6) were prepared from the epoxidation of the starting materials using the method in Example 1. As an amidine catalyst, 1, 8-diazabicyclo [5.4.0] undec-7-ene (≥99.0% GC) (DBU) was purchased from Sigma-Aldrich, Co. (St. Louis, Mo.). BDH™ Methanol (ACS grade, ≥99.8%) and 2-propanol (ACS grade, ≥99.5%) was purchased from VWR International (West Chester, Pa.). As an acid catalyst, tetrafluoroboric acid (48 wt % solution in water) was purchased from Sigma-Aldrich, Co. (St. Louis, Mo.). Tolonate IDT 70B (NCO equivalent weight=342 g/eq., 70% solids in butylacetate), an aliphatic polyisocyanate based on isophorone diisocyanate trimer (IPDI homopolymer), was provided by Perstorp Group (Cranbury, N.J.). Desmodur N 3600 (NCO equivalent weight=183 g/eq., solvent-free), an aliphatic polyisocyanate based on hexamethylene diisocyanate trimer (HDI homopolymer), was provided by Bayer MaterialScience (Pittsburgh, Pa.). All materials were used as received without further purification.

7.2 Synthesis of Sucrose Soy-Based Polyols 7.2.1 Acid-Epoxy Reaction

Acetic acid, propionic acid, and 2-ethylhexanoic acid were individually used to react with ESS to produce sucrose soyate-based polyol, in the presence of 1, 8-diazabicyclo [5.4.0] undec-7-ene (DBU) as catalyst. The reactions were carried out at 125-130° C. Acid number titration was used to monitor the reactions that would be stopped when acid number was lower than 15. Herein, 2-ethylhexanoic acid (EHA) was used as an example to synthesize polyol in the molar ratio of acid/epoxide as 0.8:1. Base-catalyzed acid-epoxy reaction was carried out in a 250 mL three-neck flask, equipped with a mechanical stirrer, thermocouple and reflux condenser. 77.38 g of ESS (0.029 mol) containing 0.312 mol epoxides and 35.99 g of EHA (0.250 mol) containing 0.250 mol carboxylic acid were added into the flask at room temperature. DBU catalyst was used at 1 wt % of total weight of ESS and EHA. 1.13 g of DBU (0.007 mol) was charged into the flask. With a mechanical stirring, the mixture of reactants and catalyst was heated to 130° C. After three and a quarter hours, the reaction was stopped with acid number as 12. A red-yellow highly viscous liquid resin was obtained as the product. Since DBU can be used as PU curing catalyst, there was no further purification after reaction. Properties of the polyols are given in Table 20.

TABLE 20

Sucrose soyate-based polyols prepared with acid-epoxy reactions

| Polyols | Acid | Acid/Epoxide (molar ratio) | Reaction time (hr) | Acid number | Reacted epoxides (%) | Hydroxyl functionality | Viscosity (mPa · s) |
| --- | --- | --- | --- | --- | --- | --- | --- |
| AA_1 | Acetic acid | 1/1 | 11.0 | 52 | 72 | 8.6 | 38,000 |
| AA_0.9 | Acetic acid | 0.9/1 | 6.5 | 37 | 70 | 8.4 | 11,940 |
| AA_0.6 | Acetic acid | 0.6/1 | 4.0 | 14 | 53 | 6.4 | 4,980 |
| PA_0.6 | Propionic acid | 0.6/1 | 5.5 | 15 | 52 | 6.2 | 12,160 |
| EHA_0.9 | 2-ethylhexanoic acid | 0.9/1 | 6.0 | 24 | 74 | 8.9 | 14,140 |
| EHA_0.8 | 2-ethylhexanoic acid | 0.8/1 | 3.25 | 12 | 72 | 8.6 | 15,100 |
| EHA_0.6 | 2-ethylhexanoic acid | 0.6/1 | 2.5 | 7.5 | 56 | 6.7 | 12,060 |
| EHA_0.4 | 2-ethylhexanoic acid | 0.4/1 | 0.5 | 1.0 | 40 | 4.8 | 5,060 |

7.2.2 Alcohol-Epoxy Reaction

Both ESS and ESSB6 were used to study the epoxide hydroxylation in alcohol-epoxy reaction. Herein, ESS was used as an example in the molar ratio of methanol/epoxide as 3:1. Acid-catalyzed alcohol-epoxy reaction was carried out in a 500 mL four-neck flask, equipped with a mechanical stirrer, thermocouple, reflux condenser and 250 mL addition funnel. 100 g of ESS (0.037 mol) containing 0.403 mol epoxides dissolved into 150 ml of isopropanol and the solution was transferred into addition funnel. 150 ml of isopropanol, 10 g of water, 40 g of methanol (1.25 mol), and 4 g of tetrafluoroboric acid (48 wt % solution in water, 0.022 mol) were charged into the flask and mixed well at room temperature. Once the mixture in flask was heated to 45° C., ESS isopropanol solution started to be dropwise added at a speed of 1 ml/min. The reaction temperature was controlled at 50° C. After the dropwise addition of ESS isopropanol solution, the reaction was held at 50° C. for 20 minutes. 5 g of sodium carbonate (0.047 mol) was added to get rid of tetrafluoroboric acid. The product solution was transferred into a beaker and dried with magnesium sulfate anhydrous for overnight to remove water. The hydrated magnesium sulfate was removed by filtration, and extra alcohols were removed by distillation at reduced pressure. The polyols prepared are listed in Table 21.

TABLE 21

Sucrose soy-based polyols prepared with alcohol-epoxy reactions

| Polyols | Methanol/epoxide (molar ratio) | Isopropanol/methanol (weight ratio) | $HBF_4$ (48 wt % in water)/Water/ESS (weight ratio) | Dropwise speed of ESS solution (ml/min) | Viscosity (cPs) |
| --- | --- | --- | --- | --- | --- |
| MESS_1 | 6/1 | 6/1 | 0.4/1/10 | 4.0 | 54,800 |
| MESS_2 | 3/1 | 6/1 | 0.4/1/10 | 1.0 | 31,600 |
| MESSB6 | 3/1 | 6/1 | 0.4/1/10 | 1.0 | 185,000 |

7.3 Polyurethane Coating Formulations

Sucrose soyate-based polyols obtained from partially epoxide opening in acid-epoxy reactions were formulated with polyisocyanate in NCO/OH stoichiometric ratio as 1.1:1. In each formulation, 80% solids content was obtained in xylene solution. Sucrose soyate-based polyols obtained from fully epoxide opening in alcohol-epoxy reactions were formulated with polyisocyanate in NCO/OH stoichiometric ratios of 1.1:1, 0.8:1, and 0.6:1. In each formulation, 80% solids content was obtained in xylene solution. PU coatings were cast on cleaned QD-36 steel panels and glass panels using a draw-down bar with a gap of 8 mils. The coatings were kept at ambient for three hours. Tack free coatings were further cured in oven at 80° C. for one hour. PU coatings on steel panels were used for ASTM tests to evaluate coating properties. PU coatings on glass panels were peeled off as thin films and used for DSC and DMA characterizations.

IDPI and HDI trimer are both aliphatic polyisocyanates. They were used to react with sucrose soyate-based polyols to prepare PU coatings in this study. The properties of PU coatings are shown in Table 22. It shows that IPDI PU coatings have better hardness and solvent-resistance, and HDI PU coatings have better flexibility and better impact and bending resistance.

The stoichiometric ratio of acid to epoxide in the acid-epoxy reaction varies the amount of hydroxyls available in the resulting polyol, which consequently affects the properties of the PU coatings. EHA produced polyols (e.g. EHA_0.4, EHA_0.6, and EHA_0.8) were cured by IPDI trimer in the same NCO/OH ratio. It shows that the higher amount of hydroxyls provides a higher degree of crosslinking, which results in the coating having better hardness and solvent resistance. Since the epoxides were fully reacted to generate hydroxyls in alcohol-epoxy reactions, the stoichiometry of NCO/OH in PU formulation was used to study its effect on the properties of coatings. It shows that the higher NCO/OH ratio results in PU coatings having better hardness and solvent resistance, but weaker impact and bending resistance because of their brittleness.

TABLE 22

Properties of polyurethane coatings

| Polyol samples | Diisocyanate trimer | NCO/OH (molar ratio) | Thickness (μm) | König pendulum hardness (s) | Pencil hardness (gouge) | Cross-hatch adhesion | MEK double rub resistance | Reverse impact (in-lb) | Mandrel bend (elongation-at-break) |
|---|---|---|---|---|---|---|---|---|---|
| EHA_0.8 | IPDI | 1.1 | 75 ± 3.4 | 164 | H | 3B | 215 | 80 | >28% |
| EHA_0.6 | IPDI | 1.1 | 71 ± 5.8 | 142 | F | 3B | 185 | >172 | >28% |
| EHA_0.4 | IPDI | 1.1 | 89 ± 5.3 | 47 | 3B | 5B | 90 | >172 | >28% |
| PA_0.6 | IPDI | 1.1 | 84 ± 9.3 | 147 | HB | 1B | 190 | 40 | >28% |
| AA_0.6 | IPDI | 1.1 | 66 ± 2.9 | 159 | 2H | 1B | 240 | 40 | <2.5% |
| AA_0.6 | HDI | 1.1 | 73 ± 6.2 | 10 | 5B | 5B | 130 | >172 | >28% |
| MESS_2 | IPDI | 1.1 | 70 ± 4.6 | 194 | B | 1B | >400 | <4 | <2.5% |
| MESS_2 | IPDI | 0.8 | 67 ± 5.6 | 179 | H | 4B | 275 | 16 | <2.5% |
| MESS_2 | IPDI | 0.6 | 66 ± 8.1 | 160 | HB | 4B | 165 | 32 | >28% |
| MESSB6 | IPDI | 1.1 | 71 ± 7.6 | 200 | B | 1B | >400 | <4 | <2.5% |
| MESSB6 | IPDI | 0.8 | 87 ± 8.5 | 192 | HB | 2B | 350 | <4 | <2.5% |
| MESSB6 | IPDI | 0.6 | 67 ± 9.6 | 172 | H | 4B | 270 | <4 | <2.5% |
| MESS_2 | HDI | 1.1 | 79 ± 5.2 | 57 | H | 5B | >400 | 8 | >28% |
| MESSB6 | HDI | 1.1 | 95 ± 6.8 | 141 | H | 5B | >400 | 32 | >28% |

The thermal and dynamic mechanical properties of PU coatings are shown in Table 23. Since DSC and DMA have different principles of measuring glass transition temperature ($T_g$), they will produce different $T_g$ values for the same sample. But the trend of $T_g$ with stoichiometry in each measurement will be very similar.

For EHA produced polyols with different stoichiometry of acid/epoxide, the values of $T_g$, E' and $v_e$ all increase with the increase of acid/epoxide ratio. For MESS_2 polyol cured with IPDI trimer in different stoichiometry of NCO/OH, the values of $T_g$, E' and $v_e$ all increase with the increase of NCO/OH ratio. PU thermoset prepared from IPDI trimer always has higher value of $T_g$, E' and $v_e$ than PU thermoset prepared from HDI trimer, in the same of NCO/OH ratio.

TABLE 23

Dynamic mechanical and thermal properties of polyurethane thin films

| Polyol samples | Diisocyanate trimer | NCO/OH (molar ratio) | DSC $T_g$ (°C) | DMA $T_g$ (°C) | E' (MPa) (@$T_g$ + 60°) | $v_e$ (×10³ mol/mm³) |
|---|---|---|---|---|---|---|
| EHA_0-8 | IPDI | 1.1 | 101 | 127 | 11.8 | 1.05 |
| EHA_0.6 | IPDI | 1.1 | 70 | 107 | 9.6 | 0.90 |
| EHA_0.4 | IPDI | 1.1 | −16 | 17 | 2.1 | 0.25 |
| PA_0.6 | IPDI | 1.1 | 72 | 115 | 8.6 | 0.79 |
| AA_0.6 | IPDI | 1.1 | 85 | 122 | 8.0 | 0.72 |
| AA_0.6 | HDI | 1.1 | 9.8 | 6.4 | 6.7 | 0.82 |
| MESS_2 | IPDI | 1.1 | 141 | 118 | 7.1 | 0.65 |
| MESS_2 | IPDI | 0.8 | 120 | 91 | 3.8 | 0.37 |
| MESS_2 | IPDI | 0.6 | 101 | 86 | 3.6 | 0.35 |
| MESSB6 | IPDI | 1.1 | 142 | 126 | 8.9 | 0.79 |
| MESSB6 | IPDI | 0.8 | 134 | 123 | 7.5 | 0.67 |
| MESSB6 | IPDI | 0.6 | 116 | 120 | 7.4 | 0.67 |
| MESS_2 | HDI | 1.1 | 47 | 62 | 19.9 | 2.07 |
| MESSB6 | HDI | 1.1 | 64 | 80 | 21.5 | 2.14 |

The claimed invention is:

1. An epoxy resin, comprising the reaction product of:
   a) a polyol having 4 or more hydroxyl groups selected from di-trimethylolpropane and polyglycidol; and
   b) an ethylenically unsaturated fatty acid, optionally a saturated fatty acid, or mixtures thereof; and
   wherein at least one ethylenically unsaturated group of the ethylenically unsaturated fatty acid is oxidized to an epoxy group.

2. The epoxy resin of claim 1, wherein the polyol having 4 or more hydroxyl groups is di-trimethylolpropane.

3. The epoxy resin of claim 1, wherein the polyol having 4 or more hydroxyl groups is polyglycidol.

4. The epoxy resin of claim 1, wherein the hydroxyls on the polyol are fully esterified by the fatty acids b).

5. The epoxy resin of claim 1, wherein about 75% to about 96% of the hydroxyls on the polyol are esterified by the fatty acids b).

6. The epoxy resin of claim 1, wherein:
   b) the ethylenically unsaturated fatty acid, optionally a saturated fatty acid, or mixtures thereof is a vegetable or seed oil fatty acid.

7. The epoxy resin of claim 6, wherein:
   b) the vegetable or seed oil is selected from corn oil, castor oil, soybean oil, safflower oil, sunflower oil, linseed oil, tall oil fatty acid, tung oil, vernonia oil, and mixtures thereof.

8. A curable coating composition, comprising:
   a) the epoxy resin of claim 1;
   b) a cationic photoinitiator;
   c) optionally, at least one diluent; and
   d) optionally, at least one pigment.

9. An object coated with the curable coating composition of claim 8.

10. A method of making the epoxy resin of claim 1, comprising the steps of:
    a) esterifying a polyol having 4 or more hydroxyl groups selected from di-trimethylolpropane and polyglycidol by reaction with an ethylenically unsaturated fatty acid, optionally a saturated fatty acid, or mixtures thereof; and
    b) oxidizing at least one ethylenically unsaturated group of the ethylenically unsaturated fatty acid to an epoxy group.

11. An ethylenically unsaturated resin, comprising the reaction product of the epoxy resin of claim 1 and at least one ethylenically unsaturated acid.

12. The ethylenically unsaturated resin of claim 11, wherein the ethylenically unsaturated acid is selected from acrylic acid, methacrylic acid, crotonic acid, maleic acid, fumaric acid, itaconic acid, and mixtures thereof.

13. A curable coating composition, comprising:
    a) the ethylenically unsaturated resin of claim 11;
    b) a free radical photoinitiator;
    c) optionally, at least one diluent; and
    d) optionally, at least one pigment.

14. An object coated with the curable coating composition of claim 13.

15. A resin having hydroxyl functionality which is the reaction product of:
the epoxy resin of claim 1 and at least one organic acid; or
the epoxy resin of claim 1 and at least one alcohol.

16. The resin of claim 15, wherein the resin having hydroxyl functionality is the reaction product of the epoxy resin and the at least one organic acid,
wherein the organic acid is selected from acetic acid, propionic acid, butyric acid, isobutyric acid, 2-ethylhexanoic acid, and mixtures thereof.

17. The resin of claim 15, wherein the resin having hydroxyl functionality is the reaction product of the epoxy resin and the at least one alcohol,
wherein the alcohol is selected from methanol, ethanol, n-propanol, n-butanol, isopropanol, isobutanol, 2-ethyl-1-hexanol, and mixtures thereof.

18. A thermoset coating composition, comprising:
a) the resin of claim 15;
b) at least one polyisocyanate;
c) optionally, at least one solvent;
d) optionally, at least one catalyst; and
e) optionally, at least one pigment.

19. An object coated with the thermoset coating composition of claim 18.

20. An epoxy-anhydride composition comprising the epoxy resin of claim 1, an acid anhydride, and a curing catalyst.

21. A curable coating composition, comprising:
a) the epoxy-anhydride composition of claim 20;
b) optionally, at least one solvent; and
c) optionally, at least one pigment.

22. An object coated with the curable coating composition of claim 21.

23. The epoxy resin of claim 1, wherein:
b) the ethylenically unsaturated fatty acid, optionally a saturated fatty acid, or mixtures thereof is a soybean oil fatty acid.

* * * * *